(12) United States Patent
Batenburg et al.

(10) Patent No.: US 9,373,180 B2
(45) Date of Patent: Jun. 21, 2016

(54) DYNAMIC TOMOGRAPHY ANGLE SELECTION

(71) Applicants: UNIVERSITEIT ANTWERPEN, Antwerp (BE); CWI, Amsterdam (NL)

(72) Inventors: Kees Joost Batenburg, Oegstgeest (NL); Jan Sijbers, Duffel (BE)

(73) Assignees: UNIVERSITEIT ANTWERPEN, Antwerpen (BE); CWI, Amsterdam (NL)

( * ) Notice: Subject to any disclaimer, the term of this patent is extended or adjusted under 35 U.S.C. 154(b) by 0 days.

(21) Appl. No.: 14/355,286

(22) PCT Filed: Oct. 30, 2012

(86) PCT No.: PCT/EP2012/071421
§ 371 (c)(1),
(2) Date: Apr. 30, 2014

(87) PCT Pub. No.: WO2013/064472
PCT Pub. Date: May 10, 2013

(65) Prior Publication Data
US 2014/0307934 A1    Oct. 16, 2014

(30) Foreign Application Priority Data
Oct. 31, 2011    (GB) .................................. 1118751.5

(51) Int. Cl.
*G06K 9/00* (2006.01)
*G06T 11/00* (2006.01)
*A61B 6/00* (2006.01)

(52) U.S. Cl.
CPC ............... *G06T 11/005* (2013.01); *A61B 6/583* (2013.01); *A61B 6/508* (2013.01); *G06T 2211/424* (2013.01); *G06T 2211/436* (2013.01)

(58) Field of Classification Search
CPC .................... G06T 2211/424; G06T 2211/436
See application file for complete search history.

(56) References Cited

U.S. PATENT DOCUMENTS

| 7,899,151 B2 * | 3/2011 | Boese et al. ................... 378/17 |
| 8,155,422 B2 * | 4/2012 | Ziegler .................. G01T 1/2985 378/4 |

(Continued)

OTHER PUBLICATIONS

Varga et al., "Projection selection algorithms for discrete tomography", Lecture Notes in Computer Science 6474 (2010) 390-401.*

(Continued)

*Primary Examiner* — Soo Park
(74) *Attorney, Agent, or Firm* — Workman Nydegger

(57) ABSTRACT

A method for determining a projection angle for use in tomographic imaging comprises obtaining projection data including at least one projection view from at least one projection angle. The at least one projection view is generated by scanning a test object with a tomographic imaging device. Each projection view comprises at least one observation value obtained at least one detection location, providing a plurality of candidate projection angles, for each candidate projection angle, calculating a function value indicative of an amount of information that may be gained by adding to the projection data a further projection view generated by scanning of the test object with the tomographic imaging device from the candidate projection angle, and selecting a candidate projection angle from the plurality of candidate projection angles taking into account the function values. A corresponding system and computer program product also is provided.

14 Claims, 15 Drawing Sheets

(56) References Cited

U.S. PATENT DOCUMENTS

| | | | |
|---|---|---|---|
| 8,825,138 B2 * | 9/2014 | Mistretta | 600/427 |
| 9,047,702 B2 * | 6/2015 | Schmitt | A61B 6/032 |
| 2011/0019791 A1 * | 1/2011 | Mueller | G01N 23/046 378/8 |
| 2014/0050302 A1 * | 2/2014 | Dennerlein | G06T 5/001 378/62 |

OTHER PUBLICATIONS

Batenburg et al., "Bounds on the Difference between Reconstructions in Binary Tomography," Field Programmable Logic and Application, Jan. 1, 2011, pp. 369-380, vol. 6607, Springer Berlin Heidelberg, Berlin.

Great Britain Search Report for corresponding Great Britain Application No. 1118751.5, Search date Feb. 28, 2012.

International Search Report for corresponding International PCT Application No. PCT/EP2012/071421, mailed Jan. 25, 2013.

Varga et al., "Projection Selection Algorithms for Discrete Tomography," Advanced Concepts for Intelligent Vision Systems, Dec. 13, 2010, pp. 390-401, Springer Berlin Heidelberg, Berlin.

Varga et al., "Projection Selection Dependency in Binary Tomography," Acta Cybernetica University of Szeged Hungary, Jun. 20, 2011, pp. 167-187, vol. 20, No. 1.

\* cited by examiner

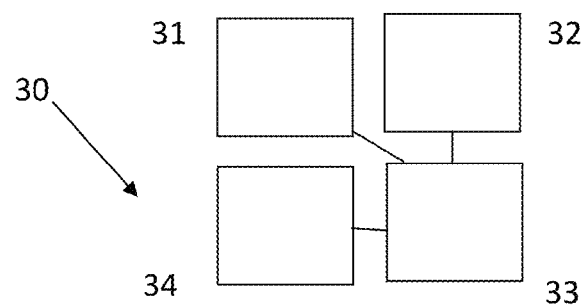
FIG. 3
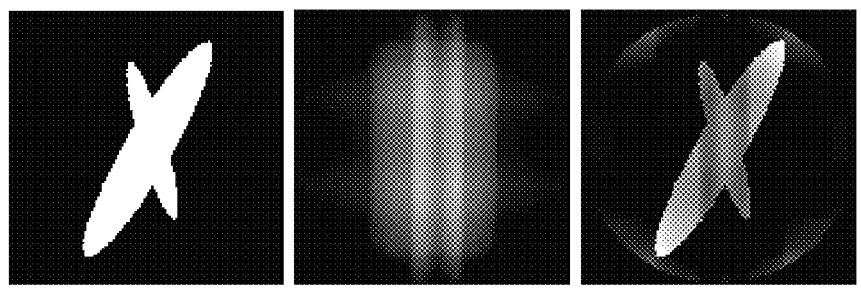
FIG. 4  FIG. 5  FIG. 6
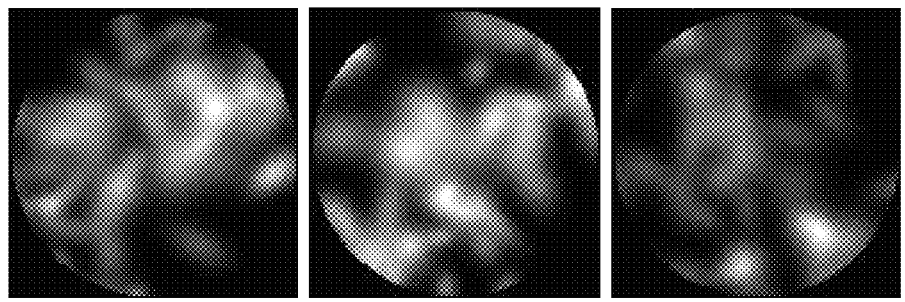
FIG. 7
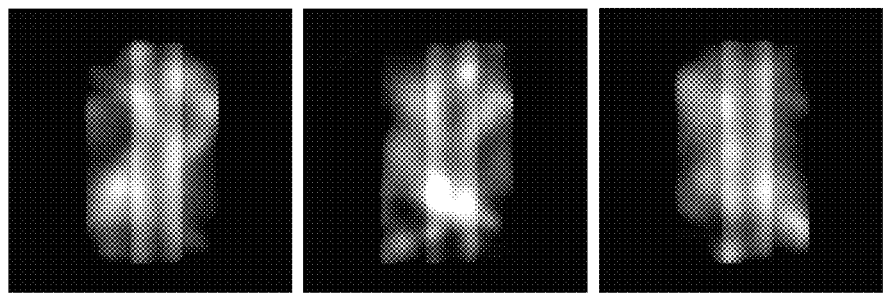
FIG. 8

DYNAMIC TOMOGRAPHY ANGLE SELECTION

FIELD OF THE INVENTION

The invention relates to the field of tomographic imaging. More specifically it relates to methods and systems for optimization of a set of projections for tomographic reconstruction.

BACKGROUND OF THE INVENTION

In tomographic imaging, penetrating waves are used to gather projection data from an object under study from multiple directions, e.g. acquired along a range of angles. Images of the object may then be reconstructed from these projections. Different tomographic imaging modalities exist for different types of penetrating waves, for example, computed tomography generally refers to X-ray tomography, single-photon emission computed tomography and positron emission tomography refer to gamma ray tomography, magnetic resonance imaging uses radiofrequent waves, and other modalities exist for visible light, electron waves and ultrasound.

In the case of computed tomography, internal structure of a patient or object may be examined non-invasively. This typically involves the collection of projection data using a detector which performs measurements relating to x-ray beams cast through the patient or object from various angles by a moving x-ray source. This allows to calculate the distribution of beam attenuation properties inside the patient or object, for example in the single plane of rotation of the moving x-ray source, or even such a distribution in a 3D volume, for example by combining a source rotating in a plane with a translation of the object of patient in a direction perpendicular to this plane.

The reconstruction of a spatial representation, e.g. a planar image or a 3D image volume, from such projection data, may be achieved by using algorithms known in the art. The Inverse Radon Transform may provide a closed-form inversion formula for this reconstruction problem, provided that projections are available for all angles. Although this assumption is clearly not satisfied in practice, an accurate reconstruction can be computed if a large number of projections are available, for a full angular range, by using the well-known Filtered Backprojection algorithm.

Most reconstruction algorithms can be subdivided in two classes: analytical reconstruction techniques, e.g. variants of filtered backprojection (FBP), and iterative algebraic methods, such as Algebraic Reconstruction Technique (ART), Simultaneous Algebraic Reconstruction Technique (SART) or Simultaneous Iterative Reconstruction Technique (SIRT). Furthermore, hybrid reconstruction methods, which may combine both types of reconstruction algorithms, are also known in the art.

Tomographic reconstruction using algebraic reconstruction algorithms does not depend on filters, and therefore circumvents difficulties in determining suitable filters for filtered backprojection in complex imaging geometries. These algorithms may typically involve iteratively adjusting an image to minimize a difference metric between simulated projection data for this image and the measured projection data. Algebraic reconstruction methods may be considered more flexible in dealing with limited data problems and noise compared to filtered backprojection. They may furthermore allow for incorporation of certain types of prior knowledge, e.g. constraints such as non-negativity of the reconstructed image, by adjusting the image between subsequent iterations. Unfortunately, the iterative nature of these methods renders them computationally more intensive.

In several applications of tomography, only few projections can be acquired. Such reconstruction problems are known as limited-data problems. In electron tomography, for example, the electron beam may damage the sample, limiting the number of projections that can be acquired. In industrial tomography for quality assurance, cost considerations impose limitations on the duration of a scan, and thereby on the number of projections.

Applying classical reconstruction algorithms such as Filtered Backprojection to limited-data problems often results in inferior reconstruction quality. Several approaches have been proposed to overcome these problems, by incorporating various forms of prior knowledge about the object in the reconstruction algorithm. Recently, advances in the field of Compressed Sensing have demonstrated high potential in obtaining a reduction of the number of required projection images by exploiting sparsity of the image with respect to a certain set of basis functions. Following a different approach, the field of discrete tomography focuses on the reconstruction of images that consist of a small, discrete set of grey values. By exploiting the knowledge of these grey values in the reconstruction algorithm, it is often possible to compute accurate reconstructions from far fewer projections than required by classical "continuous" tomography algorithms.

When reconstructing an image from a small set of projections, for example less than 20 projections, the particular set of projection angles can have a large influence on the quality of the reconstruction. The choice of the projection angles can have a crucial influence on the reconstruction quality in binary tomography, i.e., discrete tomography based on just two grey levels. Algorithms to identify optimal projection angles based on a blueprint image, which is known to be similar to the scanned object, are known in the art, e.g. such as disclosed in L. Varga, P. Balázs, A. Nagy, "Projection Selection Algorithms for Discrete Tomography," Lecture Notes in Computer Science, 6474:390-401 (2010).

SUMMARY OF THE INVENTION

It is an object of embodiments of the present invention to provide accurate tomographic imaging. It is an advantage of embodiments of the present invention that good methods and systems are provided for limited-data discrete tomographic imaging.

It is an advantage of embodiments of the present invention that good methods and systems are provided for projection selection in limited-data discrete tomographic imaging.

It is an advantage of embodiments according to the present invention that a selection of projection angle may be provided for which highly informative projection data may be obtained.

It is an advantage of embodiments according to the present invention that a selection of projection angle may be provided with little prior knowledge of the object being imaged, e.g. without prior knowledge in the form of a blueprint image or model for the object.

It is an advantage of embodiments according to the present invention that a selection of projection angle may be provided during the scanning of an object, e.g. that a sequence of angles may be provided, in which each angle is selected by taking projection data obtained for previous angles in the sequence into account.

The above objective is accomplished by a method and device according to the present invention.

The present invention relates to a method for determining a projection angle for use in tomographic imaging, the method comprising:

obtaining projection data comprising at least one projection view from at least one projection angle, the at least one projection view being generated by scanning of a test object with a tomographic imaging device, providing a plurality of candidate projection angles, for each candidate projection angle, calculating a function value indicative of an amount of information that may be gained by adding to said projection data a further projection view generated by scanning of the test object with the tomographic imaging device from said candidate projection angle, and selecting a candidate projection angle from the plurality of candidate projection angles taking into account said function values.

Each projection view may comprise at least one observation value obtained at at least one detection location.

Calculating may comprise generating a plurality of intermediate reconstructed images.

Generating may comprise reconstructing said obtained projection data with an iterative tomographic reconstruction algorithm, in which said iterative tomographic reconstruction algorithm iteratively refines a reconstruction image.

In a first iteration of said iterative tomographic reconstruction algorithm, said reconstruction image initially may comprise random data or data generated using a pseudorandom number generator algorithm.

Calculating further may comprise computing a plurality of intermediate projection data for the plurality of intermediate reconstructed images, the projection data for each intermediate reconstructed image comprising a projection view from the candidate projection angle.

Calculating may comprise calculating and combining a measure for each of the at least one intermediate projection data.

Calculating and combining may comprise determining a maximum difference over all binary images that adhere to the set of known projections for each of the at least one intermediate projection data.

The present invention also relates to a processor for determining a projection angle for use in tomographic imaging, the processor comprising an input means for obtaining projection data comprising at least one projection view from at least one projection angle, the at least one projection view being generated by scanning of a test object with a tomographic imaging device, a candidate-projection-angle obtaining means for obtaining a plurality of candidate projection angles, a calculator for, for each candidate projection angle, calculating a function value indicative of an amount of information that may be gained by adding to said projection data a further projection view generated by scanning of the test object with the tomographic imaging device from said candidate projection angle, and a selector for selecting a candidate projection angle from the plurality of candidate projection angles taking into account said function values.

The processor furthermore may be adapted for performing any of the methods for determining a projection angle.

The present invention also relates to a tomographic imaging device for tomographic imaging of objects, the tomographic imaging device comprising a processor as described above for determining a projection angle for use in the tomographic imaging.

The present invention furthermore relates to a computer program product for, if implemented on a processing unit, performing a method for determining a projection angle for use in tomography imaging as described above.

The present invention also relates to a data carrier storing such a computer program product and/or to the transmission of such a computer program product over a wide area network or local area network.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 3 illustrates a system for performing tomographic imaging according to an embodiment of the present invention.

FIG. 4 to FIG. 8 illustrates intermediate and other illustrative images as can be obtained or used in a method according to an embodiment of the present invention.

Figure 1:
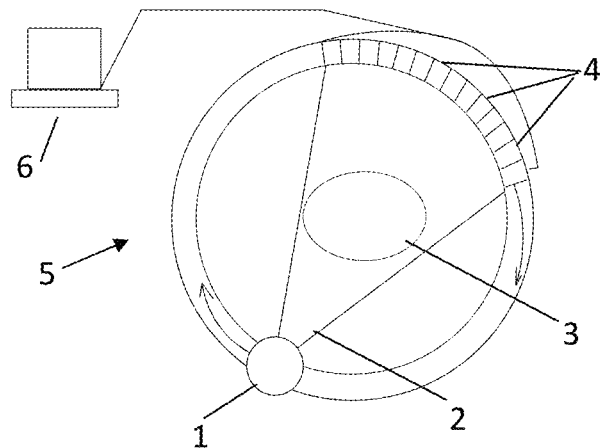
FIG. 1 shows an exemplary tomographic imaging system as can be used in embodiments according to the present invention.

The drawings are only schematic and are non-limiting. In the drawings, the size of some of the elements may be exaggerated and not drawn on scale for illustrative purposes.

Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "optimal" selection, e.g. selection of "optimal" angles, reference is made to providing an entity, e.g. a projection angle, for which a suitability measure, e.g. a quantification of information content, is optimal, e.g. maximal, or at least sub-optimal. For example, the suitability measure for this entity, e.g. projection angle, may be higher than the suitability measures for a substantial fraction of the alternatives to this entity. When considering an enumerable set of candidate entities, one of these entities may be chosen such that the suitability measure for this entity is, for example, higher than for 90% of the candidate entities, or higher than for 75% of the candidate entities, or higher than for 50% of the candidate entities. When considering an uncountable set of candidate entities, a similar reasoning applies, in that a continuous parameterization of this set may be chosen, e.g. a numeric value for an angle, ranging from 0 to $2\pi$ and representing a projection having that angle with respect to a reference orientation, from which a specific "optimal" value may be chosen such that the suitability measure for the entity associated with this value is higher than the suitability measure for entities associated with parameters within a subdomain of the parameter domain, said subdomain having a measure of extent which is substantially large, e.g. above 95%, or above 90%, or above 75%, or above 50% relative to the measure of extent of the entire parameter domain.

Where in embodiments of the present invention reference is made to an observation value, reference may be made to a measurement or detection made on an object under a projection angle.

Embodiments of the present invention relate to systems and devices that are especially suitable for use in or with a tomographic imaging system or are part of such a tomographic imaging system.

Such tomographic imaging system may for example be a computed tomography (CT) imaging or tomosynthesis imaging system, for example such systems as used in medical or veterinary examination, non-destructive testing or sample analysis. By way of illustration, embodiments of the present invention not being limited thereto, an exemplary tomographic imaging system suitable for a method or device according to an embodiment of the present invention or comprising such a device will now first be described with reference to FIG. 1, for illustrating the larger system in which a method or device according to embodiments of the present invention is used. The method typically may be implemented as a computational algorithm in a computing device of the tomographic imaging system. FIG. 1 schematically illustrates such a system 5 for tomographic imaging, also comprising a number of components conventionally present in a tomographic imaging system.

The system for example typically may comprise a radiation source 1, e.g. an x-ray source. Such x-ray source may for example comprise a vacuum tube having a tungsten anode connected to a high-voltage power supply, e.g. supplying an adjustable voltage, such as in one example a voltage up to 200 kV, or such x-ray source may for example comprise a linear accelerator for producing x-ray beams in the megavolt range. Alternatively, the radiation source 1 may comprise an electron gun for producing an electron beam, an UV, visible or IR light source, an antenna for emitting radiofrequent radiation, a gamma radiation source, a neutron radiation source or an ultrasound emitter.

This radiation source may be arranged so as to project radiation 2, e.g. an x-ray beam, gamma radiation, neutron radiation, an ultrasound wave, visible, UV or IR light or radiofrequent radiation, through a volume of interest, e.g. a volume containing a test object 3, for example a body part of a patient under study, a weld, an archeological artifact or a microscopy sample. The spectral properties of the radiation beam 2 may furthermore be conditioned by means of fixed or removable filters, e.g. metallic absorbers, for example comprising lead, tungsten andor cupper absorbers, for removing or reducing undesirable wavelengths from the beam 2. The beam may also be collimated andor focused by one or more lenses andor collimator elements as appropriate for the volume of interest. An object placed in the volume of interest, e.g. test object 3, may be supported by a suitable holding means, e.g. a sample holder or patient table, which may be constructed of material which is sufficiently radiolucent for radiation emitted by the radiation source. Such system 5 further typically may comprise a detector, such as an array of detector elements 4 in which each element measures a quantity indicative of the intensity of the radiation passing through the volume of interest, e.g. through the test object 3, along a well-defined line connecting the radiation source and this detector element 4. The radiation source 1 of such a tomographic imaging system is adapted for projecting beams through the test object along different directions, such that the detector may obtain different projection views, i.e. data obtained by measuring quantities related to beams projecting through the test object under different angles. For example, the system 5 may have an x-ray source and an arc-shaped detector array rotating around a test object to record numerous projections, as shown in FIG. 1. Power supply to the x-ray source 1 and detector may be provided by means of a slip-ring gantry, e.g. by providing a sliding electrical contact when detector and x-ray source are rotating. The system 5 may have as little as one detector element 4, which may be used to collect data in a parallel beam geometry, i.e. by combining a scanning translation movement and a rotation movement of source and detector. A small number of detector elements may be used to speed up this translation and rotation scanning by collecting multiple data points simultaneously in an approximately parallel beam geometry. Advantageous configurations for CT scanners may use a large number of detector elements to obtain data over a large arc simultaneously, thus only requiring a rotation movement of source and detector. These systems use a fan-beam geometry, which requires additional processing of the obtained data for image reconstruction. State-of-the-art CT scanners may even use a full circle arc of detector elements 4, avoiding the need to rotate the detector entirely. A test object 3 placed in the volume of interest, for example a patient, may furthermore be translated after each rotation cycle to obtain data over a range perpendicular to the rotation plane, i.e. to obtain a 3D image, e.g. a 3D image represented by a stack of 2D slices, e.g. reconstructed parallel cut plane images. Moreover, such object 3 may be moved in a continuous fashion while performing tomographic imaging, for example using a suitable holding means, such as a computer-controlled automated translation table. In this way a helical scan pattern may be obtained. The detector may even comprise multiple rows of detector elements, forming a two-dimensional detector array, to obtain data from several slices simultaneously or to allow helical scanning with a larger object translation speed as function of gantry rotation speed, thereby allowing a faster 3D image acquisition.

In certain applications, data acquisition may be limited to an angle of less than 180°. For example, in interventional radiology, CT imaging of a patient may be performed while medical personnel is positioned in close proximity to the patient, e.g. for performing a surgical intervention. In such cases, it is common practice to limit the arc wherein the radiation source is emitting to a vertically upward oriented cone, so as to shield medical personnel from backscattered radiation.

Thus, in a system 5 for tomographic imaging, the detector may be a single detector element 4, a one-dimensional array of elements or, as commonly found in such systems, a two-dimensional array of elements. The detector may be arc-shaped, as shown in FIG. 1, i.e. such that all elements of at least a single row of the detector are positioned substantially equidistant to the radiation source, or may be substantially flat. In some systems for tomographic imaging, e.g. in tomosynthesis systems used in mammography, the radiation source may rotate over a limited angle while a detector, e.g. a high resolution flat-panel direct radiography detector, translates along a single direction, thus collecting oblique projection views. Specific systems for tomographic imaging may move the radiation source over a non-circular arc.

The data obtained by a system 5 for tomographic imaging is then processed by a processing device or processor 6, e.g. a dedicated processing device programmed for calculating values indicative of beam attenuation properties of the matter contained in subvolumes of the test object. These values may then be used to form an image, e.g. a 2D image or 3D image volume, depicting variations in material properties within the test object 3, thus to obtain a reconstruction image representing this object. The processing device 6 may form an integrated part of the system 5 for tomographic imaging, or may be part of a separate computing system, e.g. only interacting with the system 5 for tomographic imaging by receiving data. Typically the method according to embodiments of the present invention will be embedded as a computational algorithm in the processing device 6. This data, e.g. projection data provided by the detector, may be transmitted over a transmission line, using wireless communications or by means of a physical data carrier, e.g. a magnetic or optical disc. The processing device 6 may furthermore be programmed for controlling the system 5, e.g. by driving the rotation of radiation source 1 andor detector 4, the translation of a test object 3 in the volume of interest and determining beam properties, e.g. peak keV, filtration and intensity. Executing such tomographic imaging protocol, i.e. applying control parameters and actuating components in a coordinated, e.g. a timed, manner allows carrying out a specific tomographic imaging using the system 5. A system 5, e.g. a system for tomographic imaging controlled by a processing device 6, may typically be used to execute diverse tomographic imaging protocols, e.g. diverse tomographic imaging protocols optimized for specific types of test objects placed in the volume of interest or for obtaining specific information from a reconstructed spatial representation of the volume of interest.

The present invention provides in devices and methods for determining optimal angles, e.g. selecting optimal angles without specific prior knowledge of the test object 3, such as for example without a blueprint image or archetypical model of this object. As the optimal angles depend on the scanned object, they may be preferably selected during the scanning procedure. In devices and methods according to embodiments of the present invention, projections may be measured sequential, e.g. one-by-one, and repeatedly a new angle, e.g. for a next projection, may be selected based on the information present in the currently available, e.g. previously gathered, projection data. Selection of projections may be based on a concise model of the available projection information, e.g. previously gathered projection data, and prior knowledge in the form of the assumed discrete, e.g. binary, character of the test object.

In a first aspect, the present invention provides in a method for determining an optimal projection parameter, e.g. a projection angle, for use in tomographic imaging, e.g. for obtaining projection data in discrete tomography.

Figure 2:
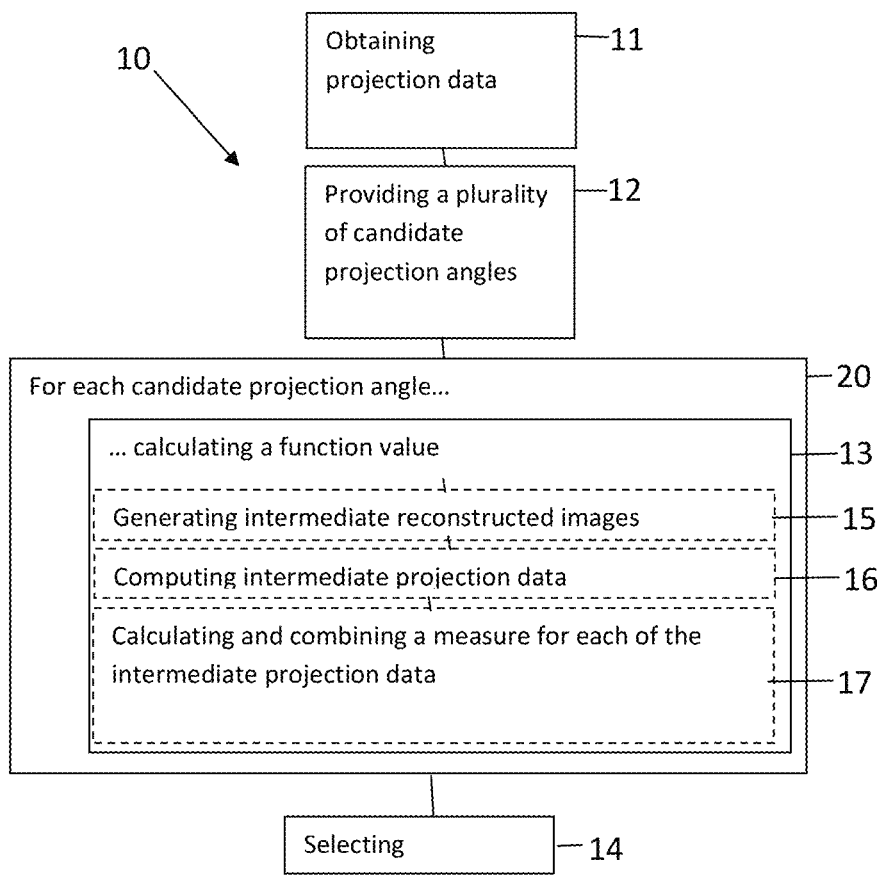
FIG. 2 illustrates a schematic overview of a method for selecting projection angles, according to an embodiment of the present invention.

An exemplary method 10 according to this first aspect of the present invention in illustrated in FIG. 2. This method 10 comprises obtaining 11 projection data. This projection data comprises at least one projection view from at least one projection angle, in which the at least one projection view is generated by scanning of a test object 3 with a tomographic imaging device 5. In some embodiments, each projection view may comprise at least one observation value obtained at at least one detection location.

The method 10 further comprises providing 12 a plurality of candidate projection parameters, e.g. projection angles, for example a set of uniformly spaced angles, e.g. at 0°, 1°, 2°, . . . , 179°. This set of projection parameters may be disjunct to the set of projection parameters corresponding to the at least one projection view in the obtained 11 projection data. For example, projection data may have been obtained for a set of projection angles A, and a set of candidate projection angles B may be provided, in such way that $A \cap B = \emptyset$.

The method 10 further comprises calculating 13 a function value for each 20 of these candidate projection parameters, e.g. candidate projection angles. This function value is indicative of an amount of information that may be gained by adding projection data obtained for the candidate projection parameter, e.g. angle, to the projection data that was obtained 11. For example, the information gained about the test object 3 being scanned with the tomographic imaging device 5 by adding a further projection view by scanning the test object 3 in accordance with this candidate projection parameter.

The method 10 comprises selecting 14 a candidate projection parameter, e.g. candidate projection angle, from the plurality of candidate projection parameters taking into account these function values. For example, the projection parameter corresponding to the highest calculated 13 function value may be selected, e.g. the parameter corresponding to an expected maximum information to be gained.

The calculating 13 may comprise generating 15 a plurality of intermediate reconstructed images. This generating 15 may comprise reconstructing the obtained projection data with an iterative tomographic reconstruction algorithm, in which the iterative tomographic reconstruction algorithm may iteratively refine a reconstruction image. In a first iteration of this iterative tomographic reconstruction algorithm, the reconstruction image may initially comprise random data or data generated using a pseudorandom number generator algorithm.

The calculating 13 may further comprise computing 16 a plurality of intermediate projection data for the plurality of intermediate reconstructed images, in which the projection data for each intermediate reconstructed image comprises a projection view from the candidate projection angle.

The calculating 13 may comprise calculating and combining 17, e.g. averaging, a measure for each of the at least one intermediate projection data.

For example, for a candidate projection angle θ, calculating 13 may comprise calculating a total information gain, e.g. according to the following steps:

1. Computing a central reconstruction x* for the projection data $p^{(\Theta)}$ taking into account a projection matrix $W^{(\Theta)}$, which consists of a stack of projection matrices $W^{(\theta)}$ for the individual projection angles Θ which were obtained in the projection data. Each projection matrix $W^{(\theta)}$ may have entries $w_{ij}^{(\theta)}$ which determine the weight of the contribution of a pixel j to a measurement i, for example representing the length of the intersection between the image pixel and the projected line.

The central reconstruction may be a reconstruction based on a known algebraic reconstruction technique. For example, the linear system $W^{(\Theta)} x = p^{(\Theta)}$ may be solved with a solver method such as Conjugate Gradient Least Squares (CGLS). The CGLS algorithm may effectively exploit the sparse structure of the projection matrix to reduce the required computation time, and may not require storage of large, dense matrices.

2. Computing a central radius, e.g. such that all solutions, such as all binary solutions, of the reconstruction problem lie on the hypersphere centered in x* with radius R. For example, by computing $$R = \sqrt{\frac{\|p^{(\Theta)}\|_1}{d} - \|x^*\|_2^2}.$$

3. Forming a new set of projection angles that include the candidate projection angle, e.g. $\Phi = \Theta \cup \{\theta\}$.

4. Looping over a predetermined number K of intermediate reconstructed images, e.g. surrogate solutions, for each of these performing the steps 4a to 4e herebelow.

4a. Generating an intermediate reconstructed image. This may comprise generating an starting image, e.g. grey level template image $c \in [0,1]^n$, which may be randomly generated from a given parameterized family of grey level images. This template image may be used as a starting point for an iterative algorithm that computes a real-valued surrogate solution $v \in S_{W^{(\Theta)}}(p^{(\Theta)}) \cap [0,1]^n$. Features present in the template images may be partially preserved within the corresponding intermediate reconstructed images, e.g. surrogate solutions, and therefore control the approximation of the current set of solutions, e.g. binary solutions.

In a possible implementation, the basic iterative reconstruction algorithm may be the iterative SIRT algorithm. In each iteration q, the reconstruction $v^{(q-1)}$ is updated, yielding a new reconstruction $v^{(q)}$, while in the first iteration $v^{(0)} = c$. This may for example be repeated for a number of Q iterations.

After each iteration, the pixels that have a negative value may be set to 0, and those that are greater than 1 may be set to 1.

4b. Forming a new set of projections that includes the projection for the candidate angle, e.g. for $\Phi = \Theta \cup \{\theta\}$. This may be a straightforward calculation of $\tilde{p}^{(\Phi)} = W^{(\Phi)} v^{(Q)}$.

4c. Calculating a new central reconstruction e.g. solving $\tilde{p}^{(\Phi)} = W^{(\Phi)} \tilde{x}$, e.g. again with the CGLS algorithm.

4d. Computing a new central radius, e.g.

$$\tilde{R} = \sqrt{\frac{\|\tilde{p}^{(\Phi)}\|_1}{d+1} - \|\tilde{x}^*\|_2^2}$$

4e. Providing an information gain for this surrogate solution, e.g. $G_i = R - \tilde{R}$.

5. Aggregating the results obtained, e.g. computing an average information gain $$G = \sqrt{\frac{1}{K}\sum_{i=1}^{K} G_i^2}.$$

It should be noted that this description is formulated for maximum clarity and may include unnecessary recomputation steps, which may be optimized in the actual implementation. Based on this algorithm for computing the total information gain, the angle selection algorithm is formed by iterating over all possible candidate angles, and selecting the angle that yields the highest total information gain.

In a second aspect, the present invention relates to a system 30 for performing tomographic reconstruction, such as the exemplary embodiment shown in FIG. 3. The system 30 comprises an input means 31 for inputting projection data produced by executing a tomographic imaging protocol for scanning a volume of interest. The latter may be an input port for receiving the measured data as well as a measurement system. Such a measurement system may for example be a measurement system for tomographic imaging as described above, embodiments of the present invention not being limited thereto.

The system 30 furthermore comprises a storage means 32 for storing a computer-implemented method according to the first aspect of the present invention. More particularly, the storage means may comprise a set of instructions to be execute by a processor or processing means for performing the computer implemented method for determining a projection angle.

The system 30 furthermore comprises a processor or processing means 33 programmed for performing said computer-implemented method for determining projection angles. The processor typically may comprise an input means for obtaining 11 projection data comprising at least one projection view from at least one projection angle, the at least one projection view being generated by scanning of a test object 3 with a tomographic imaging device (5), each projection view comprising at least one observation value obtained at at least one detection location, a candidate-projection-angle obtaining means for obtaining 12 a plurality of candidate projection angles, a calculator for, for each 20 candidate projection angle, calculating 13 a function value indicative of an amount of information that may be gained by adding to said projection data a further projection view generated by scanning of the test object 3 with the tomographic imaging device 5 from said candidate projection angle, and a selector for selecting 14 a candidate projection angle from the plurality of candidate projection angles taking into account said function values. In one aspect, the present invention also may be related to such a processor or processing means more particularly as described above.

The processor or processing means typically also may be programmed for performing the analytical reconstruction technique used therein and thus reconstructing a spatial representation of the volume of interest.

Finally, the system 30 comprises an output means 34 for outputting the spatial representation of the volume of interest.

In a third aspect, the present invention relates to a computer program product for, when executing on a processing means, for example in a device according to the second aspect of the invention, carrying out one of the methods according to the first aspect of the invention, as well as to a corresponding processing system. In other words, methods according to embodiments of the present invention may be implemented as computer-implemented methods, e.g. implemented in a software based manner. One example of a processing system may be a processing system that includes at least one programmable processor coupled to a memory subsystem that includes at least one form of memory, e.g., RAM, ROM, and so forth. It is to be noted that the processor or processors may be a general purpose, or a special purpose processor, and may be for inclusion in a device, e.g., a chip that has other components that perform other functions. Thus, one or more aspects of embodiments of the present invention can be implemented in digital electronic circuitry, or in computer hardware, firmware, software, or in combinations of them. The processing system may include a storage subsystem that has at least one disk drive andor CD-ROM drive andor DVD drive. In some implementations, a display system, a keyboard, and a pointing device may be included as part of a user interface subsystem to provide for a user to manually input information. Ports for inputting and outputting data also may be included. More elements such as network connections, interfaces to various devices, and so forth, may be included. The various elements of the processing system may be coupled in various ways, including via a bus subsystem, in the present example for simplicity a single bus, but will be understood to those skilled in the art to include a system of at least one bus. The memory of the memory subsystem may at some time hold part or all of a set of instructions that when executed on the processing system implement the steps of the method embodiments described herein.

In further aspects, the present invention relates to a data carrier for storing a filter as described above or a data carrier storing a computer program product as described above or to the transmission of a computational filter or computer program product over a wide or local area network. Such a data carrier can thus tangibly embody a computer program product or filter as described above. The carrier medium therefore may carry machine-readable code for execution by a programmable processor. The present invention thus relates to a carrier medium carrying a computer program product that, when executed on computing means, provides instructions for executing any of the methods as described above or execute the filtering function of the filter described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

In still another aspect, the present invention relates to an image or volumetric image obtained by a method according to the second aspect of the invention.

For clarity sake, theoretical principles of the present invention are provided hereinbelow, the invention not intended to be limited to these principles in any way. These theoretical principles comprise a formal model for the tomography problem, as well as several related concepts, in order to accurately define the projection selection, e.g. projection angle selection, problem. Although the formulation of the angle selection problem may characterize an optimal angle, it may not directly lead to an algorithm for computing this angle, for which requires several approximations may be required. A description of how the current set of binary solutions to the reconstruction problem may be approximated by a sampling procedure is further provided herein, leading to approximate solutions, called surrogate solutions. Further, a description of how an information gain can be approximated for a particular candidate projection angle is provided. These two approximation steps may then be combined into an algorithm for the angle selection problem according to aspects of the present invention.

This description is restricted to the reconstruction of two-dimensional images from one-dimensional projections, but may be readily generalized to higher-dimensional settings, e.g. two-dimensional projections andor three-dimensional reconstructed images, in a straightforward manner. The reconstructed image is represented on a rectangular grid of size n=w×h, e.g. having a width of w columns and a height of h rows. For setting up the tomography model, the idealized assumption is made that the unknown original object is a binary image that may be represented on this grid, even though the proposed method may still be used if the grid assumption is not satisfied. The unknown original image can be represented by a vector $\bar{v}=(\bar{v}_i)\in\{0,1\}^n$, where the entries $\bar{v}_i$ correspond to the pixel values of the reconstruction. Here, and further on in this description, a symbol decorated with an overhead bar, such as $\bar{v}$, indicates a vector or scalar having a binary domain.

Projections are measured as sets of detector values for various angles, e.g. obtained at instants while rotating around the test object. For each angle, a detector may register a parallel projection of the object. The finite set $\Theta=\{\theta_1,\ldots,\theta_d\}$ of angles for which projection data has been measured is gradually expanded: each time, an angle is selected based on the projections available so far, and the projection corresponding to this selected angle is added to the set of measurements.

The number of detector values for each projection is denoted by k. For any angle $\theta\in[0,\pi)$, the projection process in tomography can be modelled as a linear operator $W^{(\theta)}$, which maps the image $\bar{v}$ to the vector $p^{(\theta)}$ of measured data by $p^{(\theta)}=W^{(\theta)}\bar{v}$.

Figure 10:
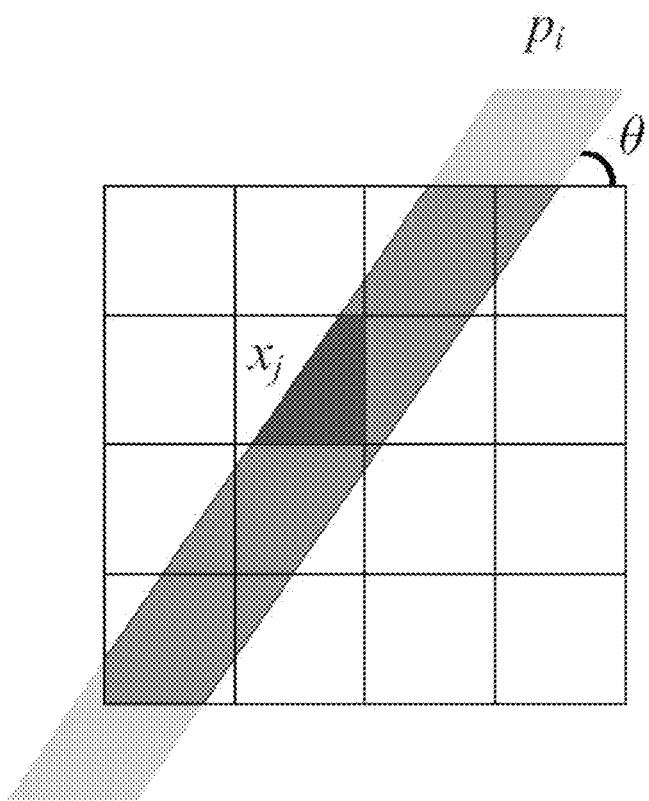
FIG. 10 demonstrates a discretized strip projection model, as can be used in embodiments according to the present invention.

The k×n matrix $W^{(\theta)}=(w_{ij}^{(\theta)})$ is called the projection matrix for angle $\theta$. The entry $w_{ij}^{(\theta)}$ determines the weight of the contribution of pixel j to measurement i, which may represent the area of the intersection between the image pixel and a strip that intersects with the image and projects onto the i'th detector pixel, such as illustrated in FIG. 10.

We may assume that each matrix $W^{(\theta)}$ has the property that $$\sum_{i=1}^{k} w_{ij}^{(\theta)} = 1$$

for all j=1, . . . , n. This property is satisfied for the strip projection model, as the total pixel weight for each projection angle is equal to the area of a pixel, which is 1. For most other projection models commonly used in tomography, such as the line model, where the weight of a pixel is determined by the length of its intersection with a line, this property is approximately satisfied, but not always exactly.

For a set of projection angles $\Theta=\{\theta_1,\theta_2,\ldots,\theta_d\}$, the projection matrix $W^{(\Theta)}$ consists of a stack of projection matrices for the individual angles, resulting in measurements $p^{(\Theta)}$ of the form:

$$p^{(\Theta)} = \begin{pmatrix} p^{(\theta_1)} \\ \vdots \\ p^{(\theta_1)} \end{pmatrix} = \begin{pmatrix} W^{(\theta_1)} \\ \vdots \\ W^{(\theta_1)} \end{pmatrix} \bar{v}.$$

For a given projection matrix $W^{(\Theta)}$ and projection data $p^{(\Theta)}=W^{(\Theta)}\bar{v}$, let $S_{W^{(\Theta)}}(p^{(\Theta)})=\{x\in R^n:W^{(\Theta)}x=p^{(\Theta)}\}$ be the set of all real-valued solutions corresponding with the projection data, and let $\bar{S}_{W^{(\Theta)}}(p^{(\Theta)})=S_{W^{(\Theta)}}(p^{(\Theta)})\cap\{0,1\}^n$ be the set of binary solutions of the system. Focusing on the case where the total number of measurements m=d×k is small with respect to n, such that the real-valued reconstruction problem is severely underdetermined.

For any two binary images $\bar{x},\bar{y}\in\{0,1\}^n$ define the image distance by $\|\bar{x}-\bar{y}\|_2$. For any set $V\subset\{0,1\}^n$, define the diameter of this set by $\mathrm{diam}(V)=\max(\|\bar{x}-\bar{y}\|_2^{\bar{x},\bar{y}\in V})$. If the diameter of V is small, all images in the set must be quite similar, whereas a large diameter indicates that strong variations occur within the set.

We now turn to the problem of angle selection. Let $\Theta=\{\theta_1, \theta_2,\ldots,\theta_d\}$ be the current set of d directions for which projection data $p^{(\Theta)}=W^{(\Theta)}\bar{v}$ of the unknown original image $\bar{v}$ have already been measured. The task is now to select the next angle for which a projection will be measured, in such a way that as much "information" as possible is gained by the new measurement.

A principal obstacle in constructing a formal model of this problem is the fact that the original image can be any element of the set $\bar{S}_{W^{(\Theta)}}(p^{(\Theta)})$, unless additional prior knowledge is available about the original image. A projection angle that yields much information for a particular element of this set, might yield very little information for other images in the same set.

To quantify the amount of information that is contained in a certain set of projections $p^{(\Theta)}$, $\mathrm{diam}(\bar{S}_{W^{(\Theta)}}(p^{(\Theta)}))$, the diameter of the set of binary solutions that adhere to all current projections, may be used. For any binary image $\bar{x}$ and set of angles $\Theta=\{\theta_1,\theta_2,\ldots,\}$, define the uncertainty of $(\bar{x}(\Theta))$ by $U(\bar{x},\Theta)=\mathrm{diam}(\bar{S}_{W^{(\Theta)}}(W^{(\Theta)}\bar{x}))$.

This uncertainty corresponds with the diameter of the set of binary images that have the same projections as $\bar{x}$ for all angles in $\Theta$. Similarly, we define the information gain of $(\bar{x},\Theta,\theta)$ by $G(\bar{x},\Theta,\theta)=U(\bar{x},\Theta)-U(\bar{x},\Theta\cup\{\theta\})$, which can be used as a measure for the information gained by measuring the projection for angle $\theta$, if the projections for all angles in $\Theta$ are already available and $\bar{x}$ is the original object. Clearly, the information gain is always nonnegative, and is zero for any $\theta$ that is already in $\Theta$.

This concept may be extended to the average information gain of a set of binary images $V \subset \{0,1\}^n$, by defining $$G(V, \Theta, \theta) = \sqrt{\frac{1}{|V|} \sum_{\bar{x} \in V} G(\bar{x}, \Theta, \theta)^2}.$$

Having defined these concepts and notation, the angle estimation problem may be formulated as follows: if $\Theta = \{\theta_1, \theta_2, \ldots, \theta_d\}$ is the current set of d directions for which projection data $p^{(\Theta)} = W^{(\Theta)} \bar{v}$ of the unknown original image $\bar{v}$ have already been measured, find $$\theta_{d+1} = \arg\max_{\theta \in [0,\pi)} G(\bar{S}_{W^{(\Theta)}}(p^{(\Theta)}), \Theta, \theta).$$

This problem can be interpreted as follows: we seek the new projection angle $\theta_{d+1}$, such that the total information gained by adding this angle, over all binary images that adhere to the current set of known projections, is maximized.

Although this problem effectively captures all concepts involved in the angle estimation problem, its formulation is not suitable for direct translation into an algorithm. It is well known that the problem of reconstructing binary images from more than two projections is NP-hard, which makes it unfeasible to enumerate the set of binary solutions for a large-scale reconstruction problem. Such an enumeration is needed to compute the total gain over all binary solutions that adhere to the available projections, and to compute the diameter of the solution set within the computation of the gain for an individual image.

To construct an algorithm based on the concepts in this problem formulation, three approximations may be used. Firstly, the summation over all binary solutions within the computation of the total gain may replaced by a summation over a set of surrogate solutions, which are real-valued solutions to the reconstruction problem for which all pixel values are in the interval [0, 1]. Secondly, within the computation of the gain for an individual image, the diameter of the binary solution set may approximated by an upper bound of the diameter. Such an upper bound may be used effectively as a substitute for the true diameter, as may be suggested by previously published experimental results in the field. Finally, the continuous domain of the candidate angle $\theta_{d+1}$ is replaced by a finite discretization, e.g. having an angular step size of 1 degree.

Turning to the first approximation mentioned hereinabove, as the number of binary images that adhere to the currently available projections can be exponential in n, a complete enumeration of all such images to evaluate the information gain in the selection problem as formulated hereinabove may be unfeasible.

To approximate the evaluation of $G(\bar{S}_{W^{(\Theta)}} p^{(\Theta)}), \Theta, \theta_{d+1})$, the total information gain for a set of surrogate solutions, which are not necessarily binary, is computed. The surrogate solutions are real-valued solutions of the reconstruction problem for which all entries have values in the interval [0, 1]. These surrogate solutions are then used as samples to represent the true set $\bar{S}_{W^{(\Theta)}}(p^{(\Theta)})$ of binary solutions.

The starting point for generating a surrogate solution is a grey level template image $C \in [0,1]^n$, which is randomly generated from a given parameterized family of grey level images. The choice of the image family to be used for the template images may directly influence the sampling pattern of the surrogate solutions. The template image is used as a starting point for an iterative algorithm that computes a real-valued surrogate solution $v \in S_{W^{(\Theta)}}(p^{(\Theta)}) \cap [0,1]^n$. The generation of template images can be considered as sampling from a prior distribution, where the particular family of template images determines the prior distribution. Features present in the template images are partially preserved within the corresponding surrogate solutions, and therefore control the approximation of the current set of binary solutions.

In a possible implementation, the basic algorithm for computing a real-valued surrogate solution may be the iterative SIRT algorithm, defined as follows. Let $v^{(0)} = c$. For $q = 1, 2, \ldots$, let $r^{(q)} = p^{(\Theta)} - W^{(\Theta)} v^{(q-1)}$ be the projection difference before the q'th iteration. In each iteration q, the current reconstruction $v^{(q-1)}$ is updated, yielding a new reconstruction $v^{(q)}$, as follows:

$$v_j^{(q)} = v_j^{(q-1)} + \frac{1}{\sum_{i=1}^m w_{ij}^{(\Theta)}} \sum_{i=1}^m \frac{w_{ij}^{(\Theta)} r_i^{(q)}}{\sum_{k=1}^n w_{ik}^{(\Theta)}},$$

with m the total number of detector measurements. It can be shown that for a consistent system of equations, the SIRT-algorithm converges to the solution $\hat{v}$ that is closest to the initial image $v^{(0)}$ in the Euclidean sense. Here, an adaptation of this algorithm is used which confines the solution to the interval [0, 1]. After each iteration, the pixels that have a negative value are set to 0, and those that are greater than 1 are set to 1. As this truncation operation is the projection onto a convex set, the resulting algorithm still converges to a solution of the tomography problem, yet it is not guaranteed to be the solution that is closest to the initial image.

Turning to the second approximation mentioned hereinabove, once a surrogate solution v has been computed, the information gain needs to be computed for each of the candidate angles. We recall that the information gain for a candidate angle $\theta$ is defined as the difference between the diameter of the current set of binary solutions, and the diameter of the set of binary images that have the same projections as v for all angles $\Theta \cup \{\theta\}$. An upper bound on the diameter of $\bar{S}_{W^{(\Theta)}}(p^{(\Theta)})$ will now be described, which can be used effectively as a substitute for the true diameter.

An important concept in the derivation of this upper bound is the central reconstruction: the shortest real-valued solution in $S_{W^{(\Theta)}}(p^{(\Theta)})$, in the Euclidean sense. Hereinafter, this solution is denoted by $x^*$. As the central reconstruction corresponds to the projection of the origin onto the linear manifold containing the real-valued solutions, it can be computed by standard linear algebra methods. In the here presented implementation, an iterative Krylov subspace method is used for solving the system $W^{(\Theta)} x = p^{(\Theta)}$, called Conjugate Gradient Least Squares (CGLS). The CGLS algorithm can effectively exploit the sparse structure of the projection matrix to reduce the required computation time, and does not require storage of large, dense matrices. Apart from numerical errors, applying CGLS to the system $W^{(\Theta)} x = p^{(\Theta)}$ results, after convergence, in the computation of $x^*$.

The Euclidean norm of any binary solution of $W^{(\Theta)} x = p^{(\Theta)}$ is completely determined by $p^{(\Theta)}$: if $\bar{x} \in \bar{S}_{W^{(\Theta)}}(p^{(\Theta)})$, then $$\|\bar{x}\|_2^2 = \frac{\|p^{(\Theta)}\|_1}{d}.$$

This property follows from two basic observations summing the measured values over all detector elements for a projection angle yields the sum of the pixel values in the image, and the squared Euclidean norm of a binary image is equal to the sum of its pixel values.

By definition of the $L_1$ norm, $\|p^{(\Theta)}\|_1 = \Sigma_{i=1}^m |p_i^{(\Theta)}| = \Sigma_{i=1}^m p_i^{(\Theta)}$, since $p_i^{(\Theta)} \geq 0$ for i=1, ..., m. Also, $\Sigma_{i=1}^m p_i^{(\Theta)} = \Sigma_{i=1}^m (\Sigma_{j=1}^n w_{ij}^{(\Theta)} \bar{x}_j) = \Sigma_{j=1}^n (\Sigma_{i=1}^m w_{ij}^{(\Theta)}) \bar{x}_j = \Sigma_{j=1}^n d\bar{x}_j$, and therefore $\|p^{(\Theta)}\|_1 = d\Sigma_{j=1}^n \bar{x}_j$. As $\bar{x} \in \{0,1\}^n$, we have $$\|\bar{x}\|_2^2 = \|\bar{x}\|_1 = \sum_{j=1}^n \bar{x}_j = \frac{\|p^{(\Theta)}\|_1}{d}.$$

All binary solutions of the reconstruction problem lie on the hypersphere centered in x* with radius R, in which the central radius is defined by $$R = \sqrt{\frac{\|p^{(\Theta)}\|_1}{d} - \|x^*\|_2^2};$$

if $\bar{x} \in S_{W^{(\Theta)}}(p^{(\Theta)})$, then $$\|\bar{x} - x^*\|_2 = \sqrt{\frac{\|p^{(\Theta)}\|_1}{d} - \|x^*\|_2^2}.$$

From the definition of x* we have $(\bar{x}-x^*) \in N(W)$, and $x^* \perp (\bar{x}-x^*)$. Applying Pythagoras' Theorem and the expression for the Euclidean norm derived hereinabove, yields $$\|\bar{x} - x^*\|_2^2 = \frac{\|p^{(\Theta)}\|_1}{d} - \|x^*\|_2^2.$$

Supposing the existence of at least two different binary solutions, this result may enable the derivation of an upper bound for the number of pixel differences between two solutions:

let $\bar{x}, \bar{y} \in S_{W^{(\Theta)}}(p^{(\Theta)})$, then $\|\bar{x}-\bar{y}\|_2 \leq \|\bar{x}-x^*\|_2 + \|\bar{y}-x^*\|_2 = 2R$.

The upper bound thus obtained can be computed simply by evaluating the radius R of the sphere centred in x* that contains the binary solutions. It may be remarked that there is no guarantee that different binary solutions are indeed so far apart, or even that one or more binary solutions exist. Still, experimental results demonstrate that the radius R correlates surprisingly strong with the reconstruction error that is made when reconstructing a binary image from a small number of projections. It can therefore serve as a substitute of the true diameter, to calculate an amount which is indicative of information present in the projection data.

In the following discussion, for illustrative purposes and not intended to be limiting the invention in any way, an example of an embodiment of the present invention will be presented. To illustrate the concepts of surrogate solutions and information gain, a binary phantom image $\bar{x}$ that has two principal orientations is depicted in FIG. 4.

Suppose that the projection of this image has already been measured for the horizontal and vertical directions. The central reconstruction x* corresponding to these two projections is shown in FIG. 5. The difference image $\|\bar{x}-x^*\|$ is shown in FIG. 6. The Euclidean norm of this image corresponds with the central radius, and therefore provides an upper bound on the diameter of the set of binary solutions that adhere to the two given projections.

By way of illustration, embodiments of the present invention not being limited thereto, an example of generating template images is described here. The class of images from which the template images are sampled can have an impact on the sampling of surrogate solutions. It was found that for the type of phantom images considered here, each template image advantageously contains a substantial number of randomly generated "features", representing a variety of orientations. In particular, for all experimental results presented in the present example, the template images are generated as a superposition of 2D Gaussian blobs. Each template image is formed by adding the intensity for 50 such blobs, where the orientation of the blob is chosen randomly and the standard deviation along both the major and minor axis are chosen randomly between 3 and 10 pixels. Examples of such template images are shown in FIG. 7. The sample templates are set to 0 outside the circular reconstruction region. The surrogate solutions corresponding to these random template images are shown in FIG. 8 in corresponding order. The surrogate solutions adhere to the two available projections and contain only pixel values in the interval [0, 1]. Although the surrogate solutions share the same horizontal and vertical projections, there are substantial differences between the three images.

Note that the central reconstruction itself is not suitable to be used as a surrogate solution. The central reconstruction is the shortest solution that adheres to the available projections, using the Euclidean metric. If one would compute the projections of the central reconstruction for all candidate angles and determine the information gain for each of these angles, this gain will also be 0, as the central reconstruction does not change: the current central reconstruction will also be the shortest solution of the new equation system that is formed by adding the extra projection.

Figure 9:
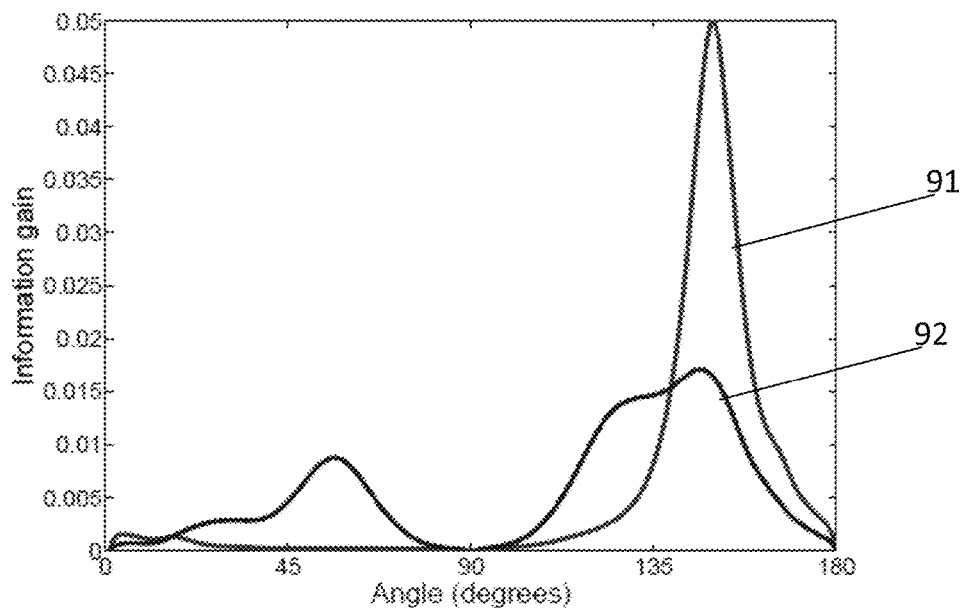
FIG. 9 illustrates possible information gain for different candidate angles, based on a true phantom image or based on surrogate solutions, illustrating features of embodiments according to the present invention.

For each candidate angle, and for each surrogate solution, the information gain can now be computed by first computing the projection of the surrogate solution for the new angle, and then computing an upper bound for the diameter of the set of binary solutions for the reconstruction problem that is formed by adding this projection to the current measured data. FIG. 9 shows plots of the total information gain G for each candidate angle θ, the first plot 91 being based on knowledge of the true phantom image, and the second plot 92 being based on the three surrogate solutions. We observe that even though the phantom image is hardly recognizable in the three surrogate solutions, the peak of the information gain for the phantom can also be seen in the information gain for the set of surrogate images.

As a further illustrative example, simulation experiments are described hereinbelow in order to demonstrate the ability of methods according to embodiments of the present invention to select favourable projection angles. The quality of the selected angles with respect to the actual unknown object is clarified, based on the assumption that a good angle selection scheme should lead to an accurate reconstruction of the object from fewer angles than the number of angles that would be needed for the standard equi-angular scheme. However, it may be noted that this assumption should be framed in a statistical point-of-view: in particular cases, an angle for which limited information is gained with respect to the actual unknown object, might yield significantly more information for other candidate solutions that adhere to the currently known projections.

Figure 11:
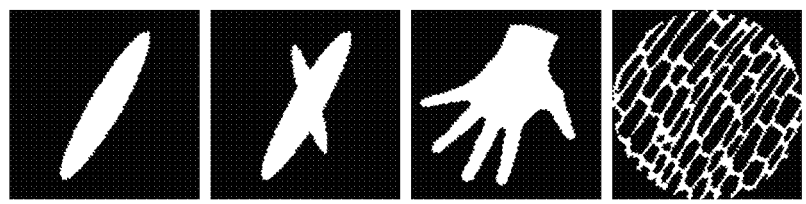
FIG. 11 shows four phantom images used in simulation examples using methods according to embodiments of the present invention.

These examples are based on simulated projection data obtained by computing the projections of the test images, commonly referred to as phantoms, shown in FIG. 11. These phantoms comprise respectively, from left to right, a single ellipse, a double ellipse, a hand phantom and a foam phantom. All phantoms have a size of 128×128 pixels. The reconstruction area, however, was confined to the pixels within a central disk having a radius of 64 pixels.

In the simulation examples presented hereinbelow, the proposed angle selection algorithm is followed as it chooses consecutive angles for a single phantom. Each time a new angle has to be selected, the following error measures are evaluated for each candidate angle θ: the information gain G($\bar{x}$θ) for the actual phantom image $\bar{x}$ (also referred to as the Phantom gain), the mean information gain G(V,θ) for a set of surrogate solutions V (also referred to as the Sample gain), and the relative number of misclassified pixels rNMP for a thresholded CGLS (TCGLS) reconstruction, with threshold 0.5, obtained after adding the projection for angle θ.

When interpreting the results, two comparisons may be focused on. Firstly, if the (local) maxima 51 of the information gain for the surrogate solutions coincide with the maxima 52 for the information gain based on the phantom, the angle selection algorithm will choose an angle that yields substantial information about the phantom, as it results in a relatively strong reduction of the central radius. Secondly, the positions of the extremal points of the information gain curve for the phantom should correspond with the extremal points of the rNMP curve, such that local maxima 52 of the gain curve correspond with local minima 53 of the rNMP curve, and vice versa. If this property is approximately satisfied, a large information gain, as previously defined herein, will correspond with a relatively large reduction of the reconstruction error for the TCGLS algorithm. The sample gain variation is shown by area 59.

In FIG. 12a to FIG. 15d, the information gain computed using the phantom image (phantom gain) as well as the information gain computed without the knowledge of the phantom image (sample gain) are plotted for each angle in the range 1° to 180° (in steps of 1 degree), ad for each phantom image. FIG. 12a to FIG. 15d correspond respectively to the four phantom images depicted from left to right in FIG. 11. The phantom gain is shown along with its variation (shaded area), indicating the range from the minimum until the maximum sample bound. Furthermore, the rNMP of the CGLS reconstructions for each candidate angle is shown in the same plot. The first graph FIG. 12a corresponds to d=1, the second graph FIG. 12b to d=2, the third graph FIG. 12c to d=3 and the fourth graph FIG. 12d to d=4. In FIG. 13a to FIG. 13d, the first graph FIG. 13a corresponds to d=2, the second graph FIG. 13b corresponds to d=3, the third graph FIG. 13c corresponds to d=4 and the fourth graph FIG. 13d corresponds to d=5.

Figure 12A:
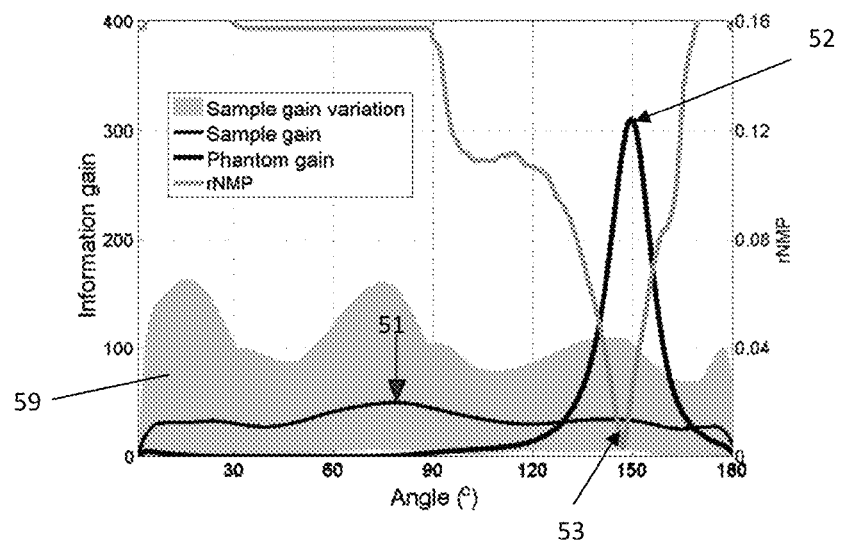
FIG. 12a to FIG. 12d shows graphs of information gain G and relative number of misclassified pixels rNMP as a function of the projection angle $\theta_{d+1}$ for the leftmost phantom shown in FIG. 11.
Figure 12B:
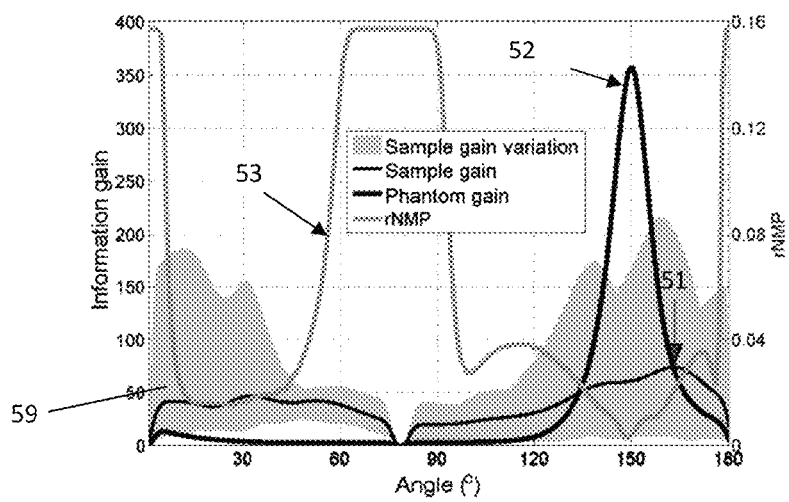
Figure 12C:
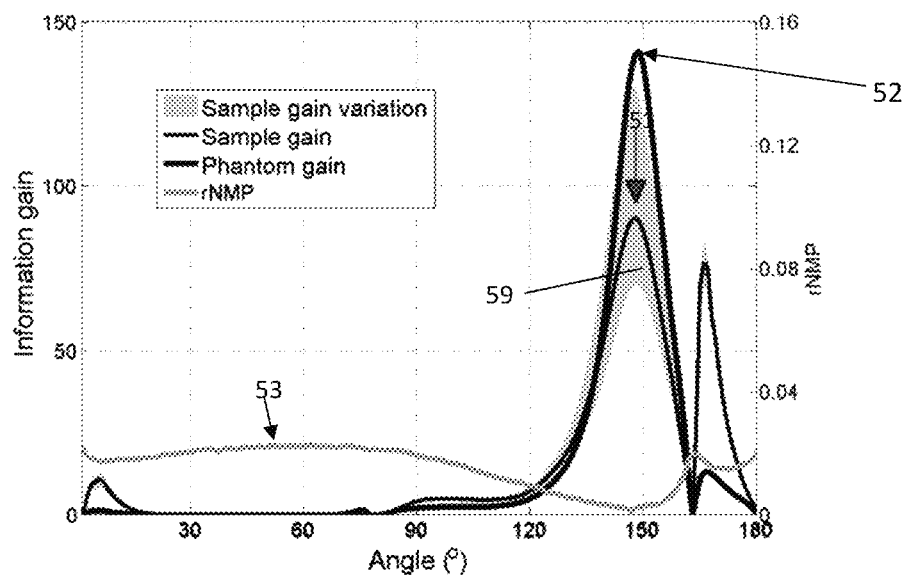
Figure 13A:
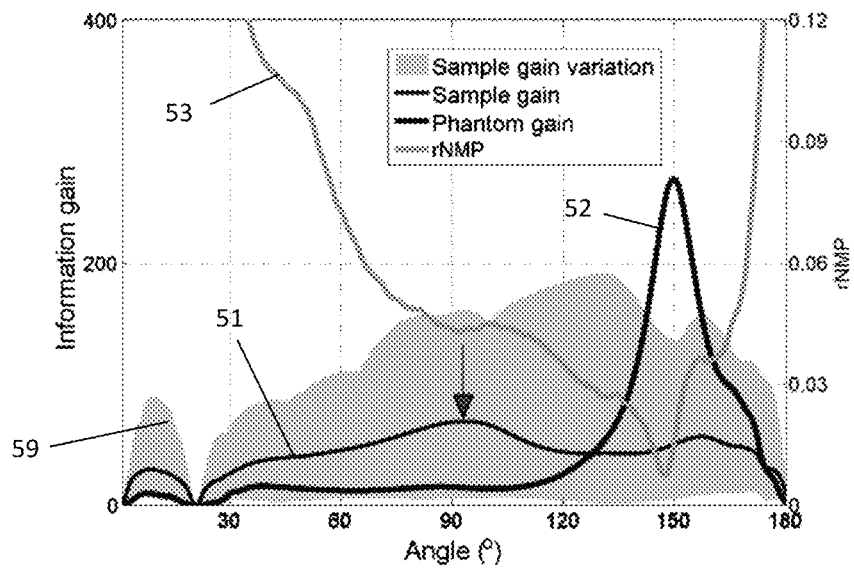
FIG. 13a to FIG. 13d shows graphs of information gain G and relative number of misclassified pixels rNMP as a function of the projection angle $\theta_{d+1}$ for the centre-left phantom shown in FIG. 11.
Figure 13B:
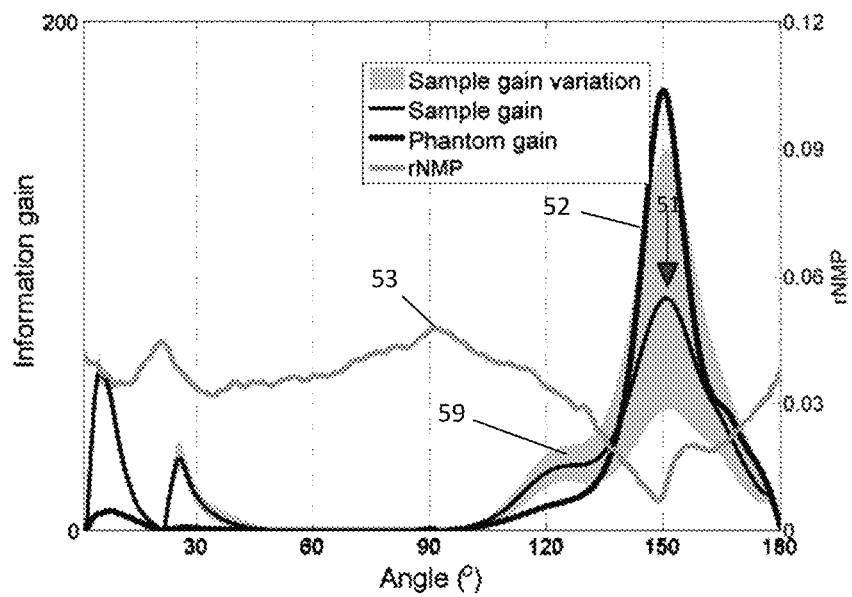

If the number of projections is very small (two or less for the present example), the dynamic angle selection does not select the angle that corresponds to the maximum phantom information gain, see FIG. 12a and FIG. 12b and FIG. 13a. This can be explained by the fact that for d smaller than or equal to 2, the reconstruction problem is highly underdetermined, and there are large differences between the surrogate solutions. An angle choice that is optimal with respect to the phantom does not appear to be optimal with respect to the combined set of surrogate solutions.

Figure 12D:
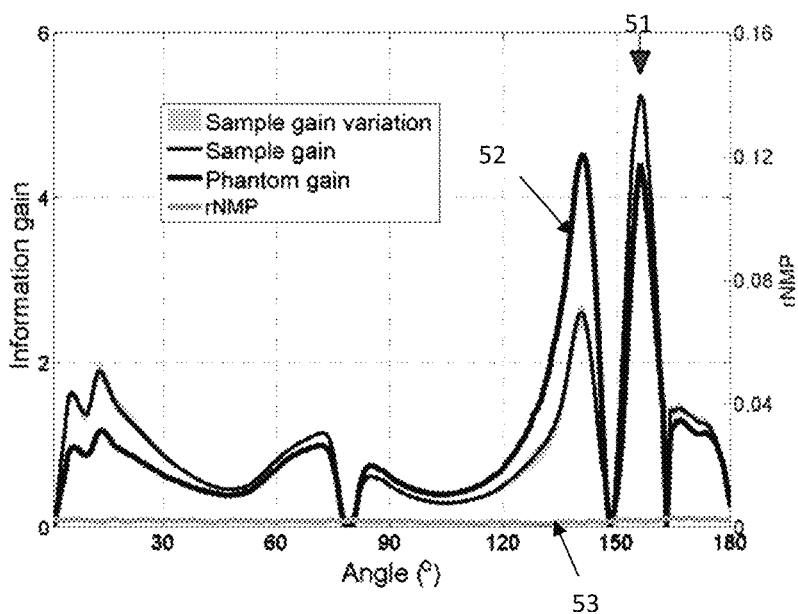
Figure 13C:
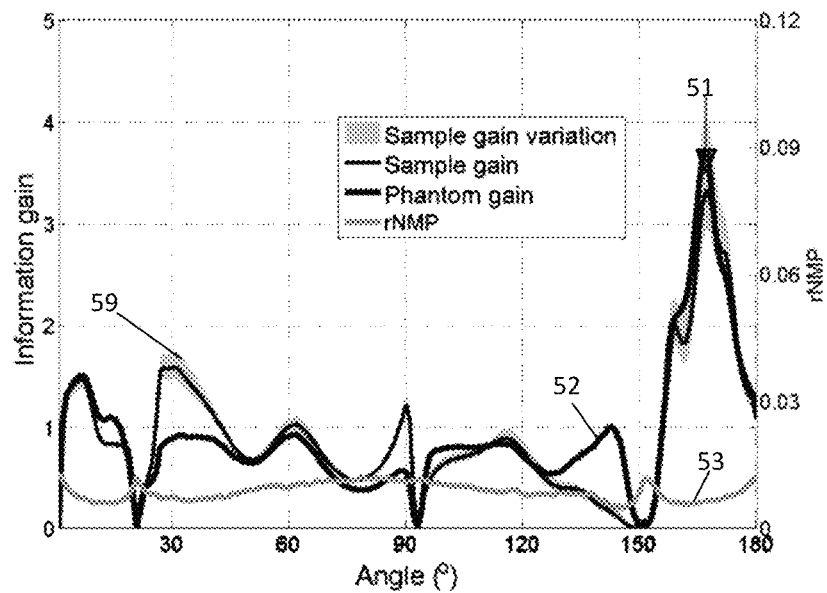
Figure 13D:
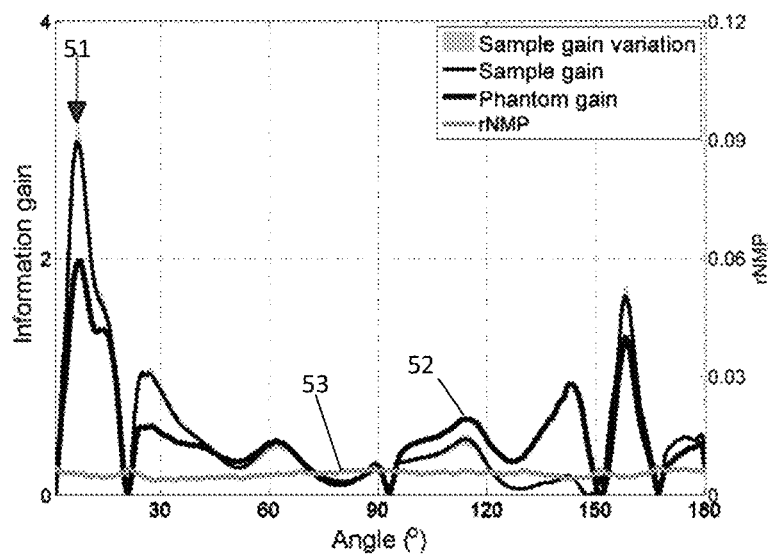

However, for more than 2 projections, the correlation between the sample gain curve and the phantom gain curve is much higher for both Phantoms 1 and 2. Indeed, for three projections, the dynamic angle selection selects an angle that closely matches that of the maximum phantom gain, see FIG. 12c and FIG. 13b. Similar observations can be made for 4 or more projections, as is shown in FIG. 12d, FIG. 13c and FIG. 13d.

Figure 14A:
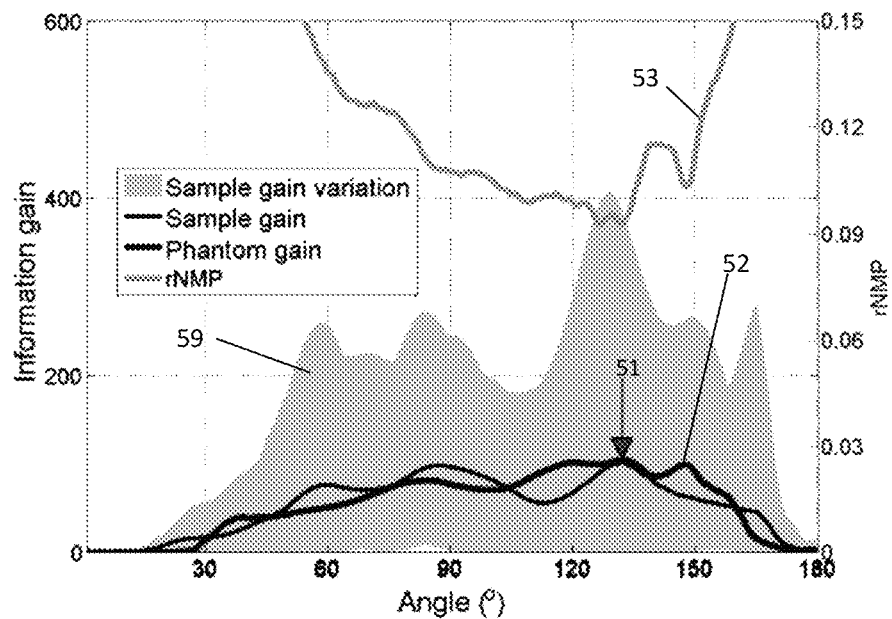
FIG. 14a to FIG. 14d shows graphs of information gain G and relative number of misclassified pixels rNMP as a function of the projection angle $\theta_{d+1}$ for the centre-right phantom shown in FIG. 11.
Figure 14B:
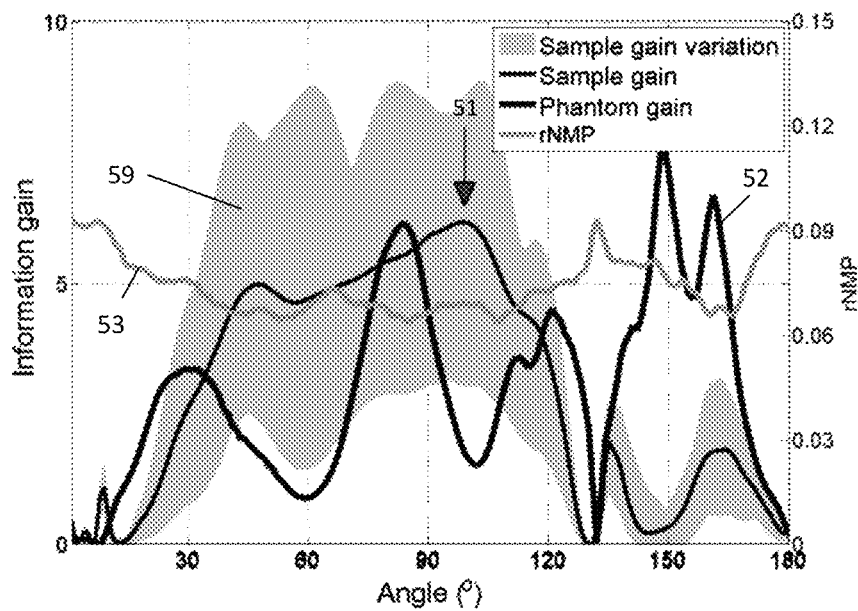
Figure 14C:
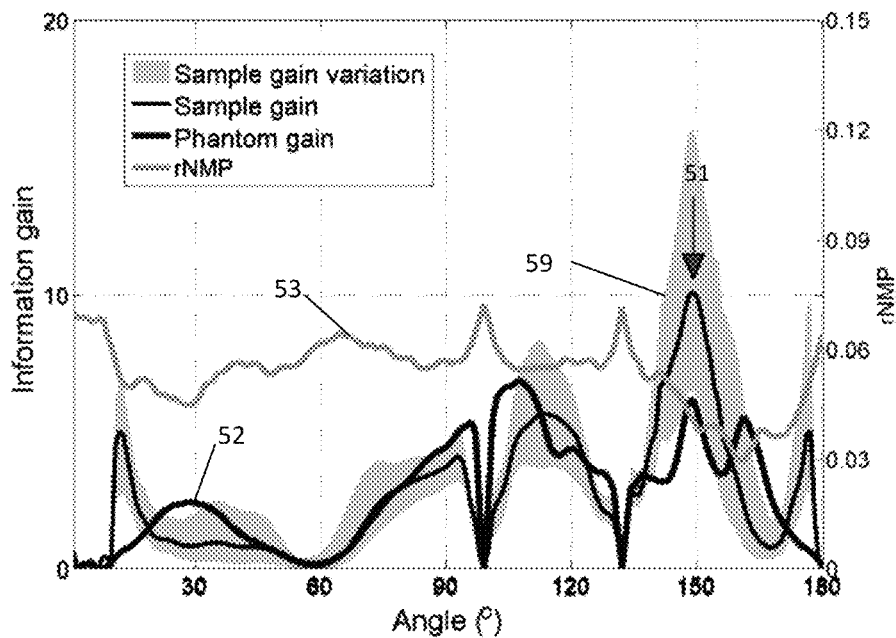
Figure 14D:
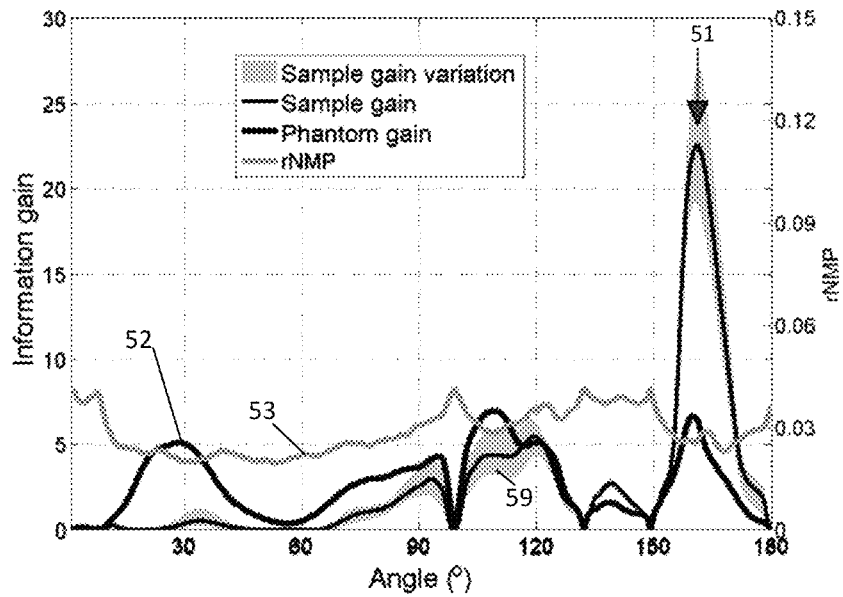
Figure 15A:
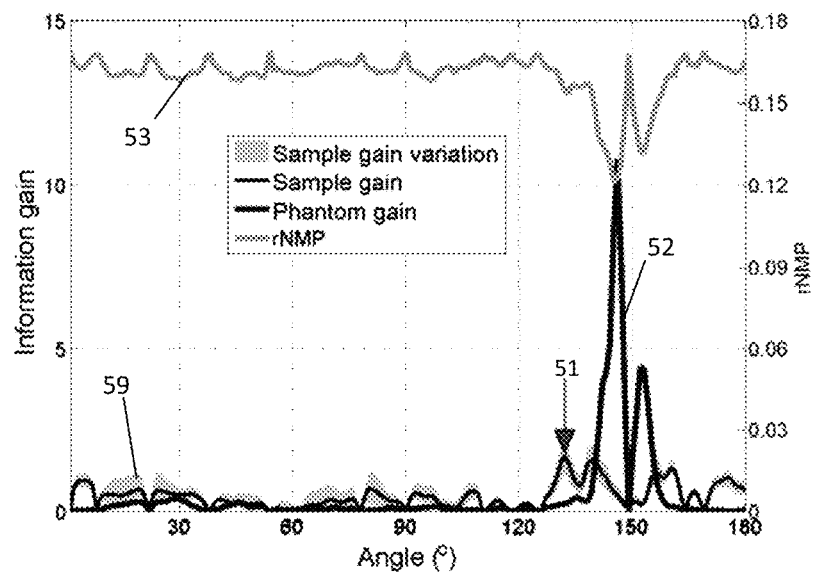
FIG. 15a to FIG. 15d shows graphs of information gain G and relative number of misclassified pixels rNMP as a function of the projection angle $\theta_{d+1}$ for the rightmost phantom shown in FIG. 11.
Figure 15B:
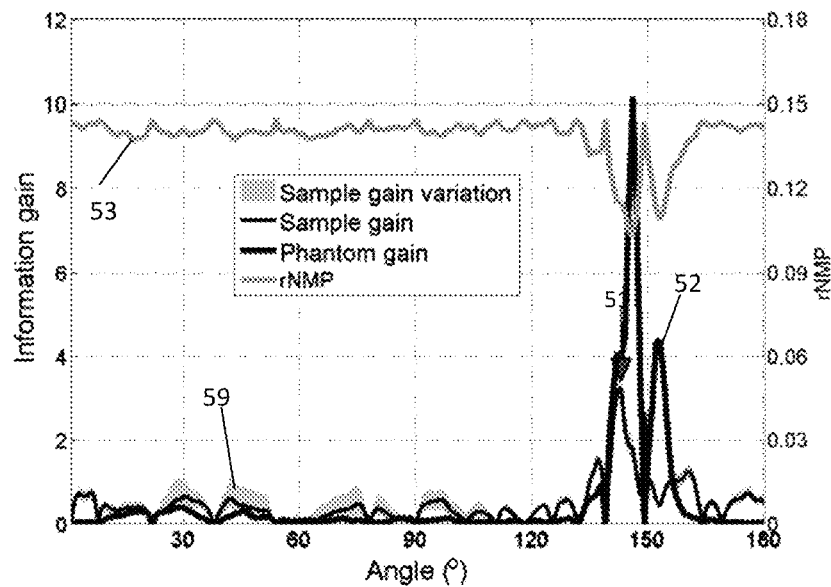
Figure 15C:
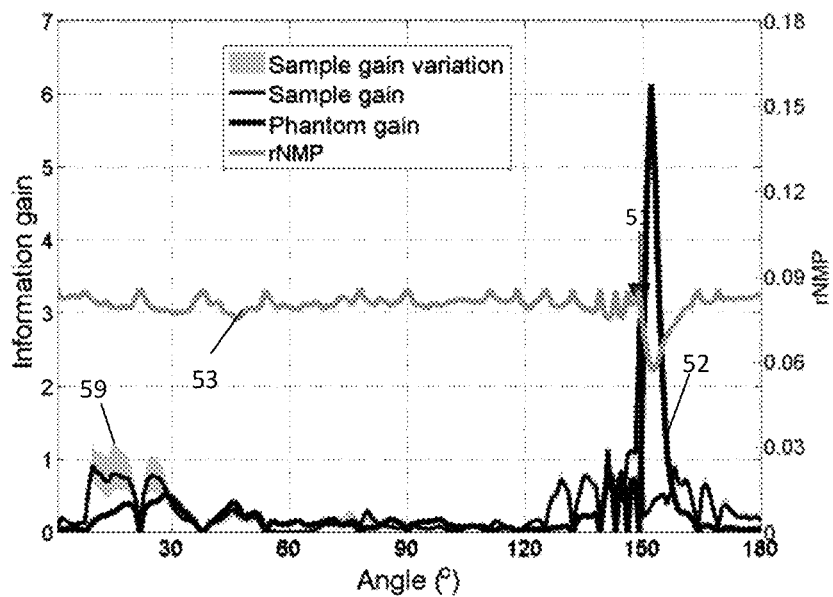
Figure 15D:
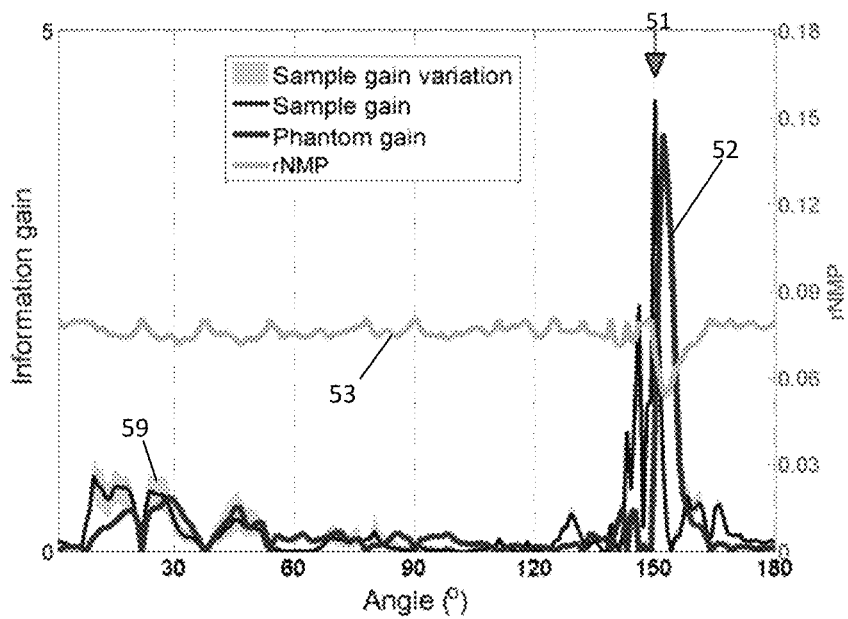
Figure 16A:
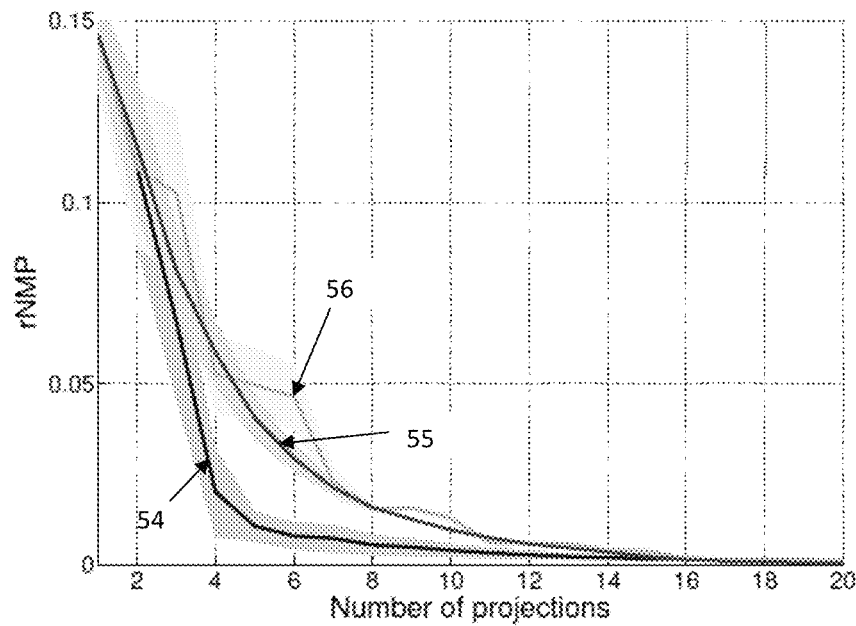
FIG. 16a to FIG. 16d shows graphs of the relative number of misclassified pixels rNMP as a function of the number of projections d for the four phantoms shown in FIG. 11.
Figure 16B:
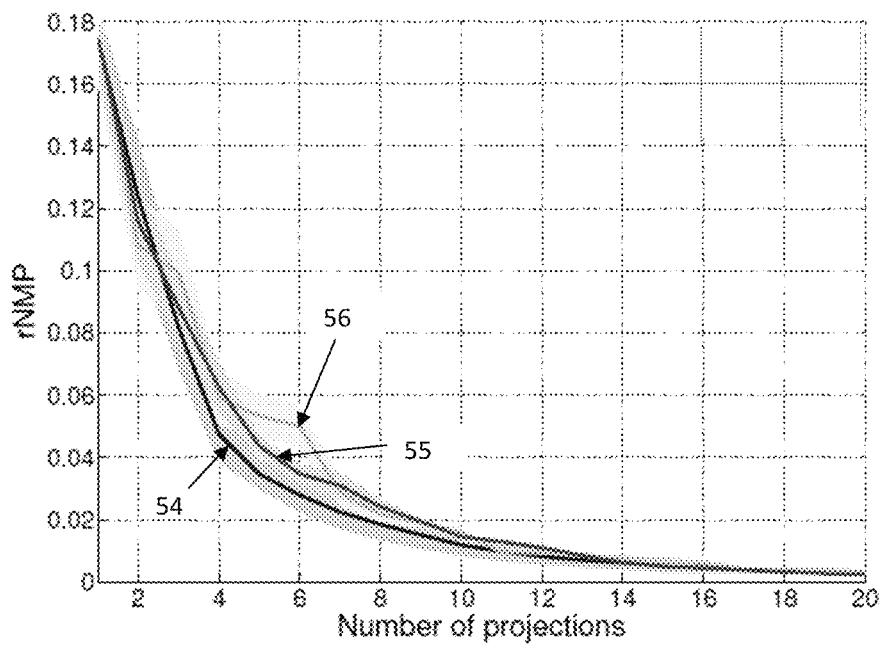
Figure 16C:
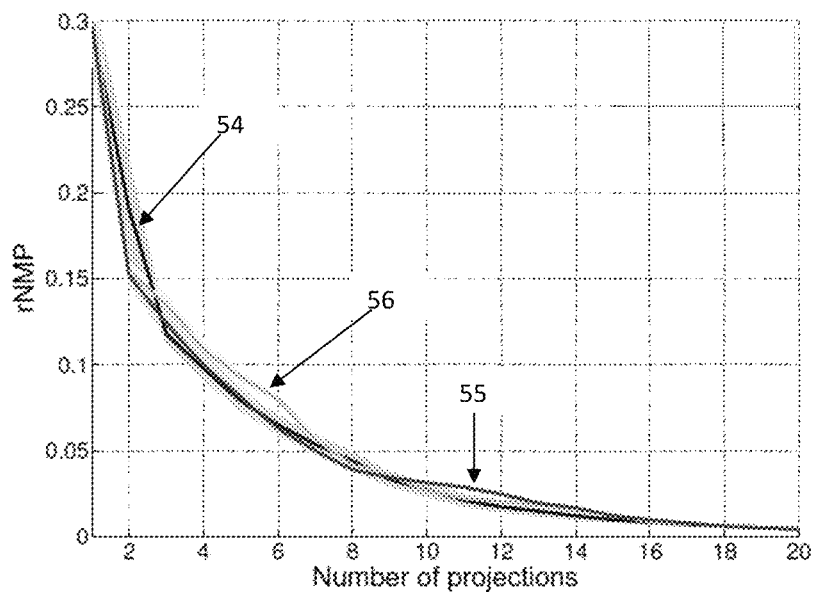
Figure 16D:
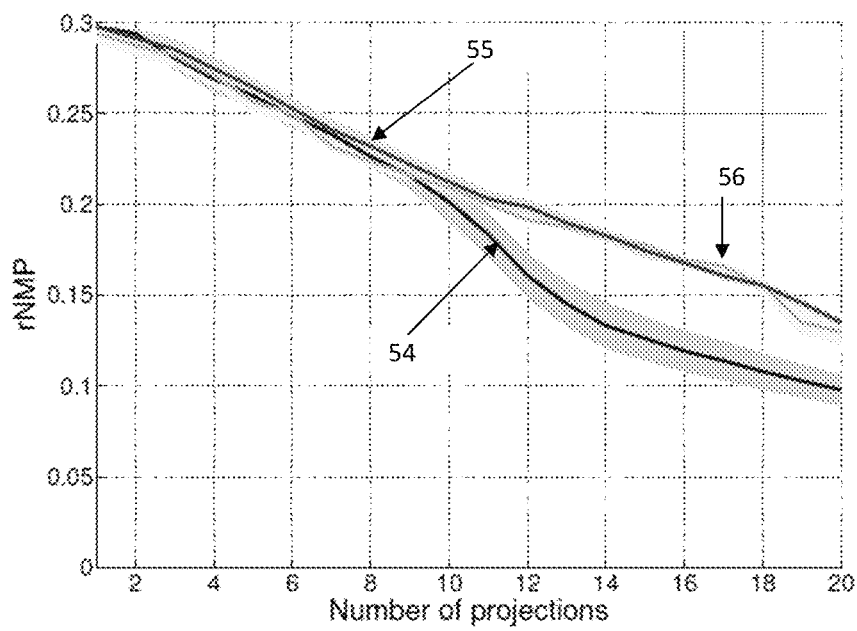
Figure 17A:
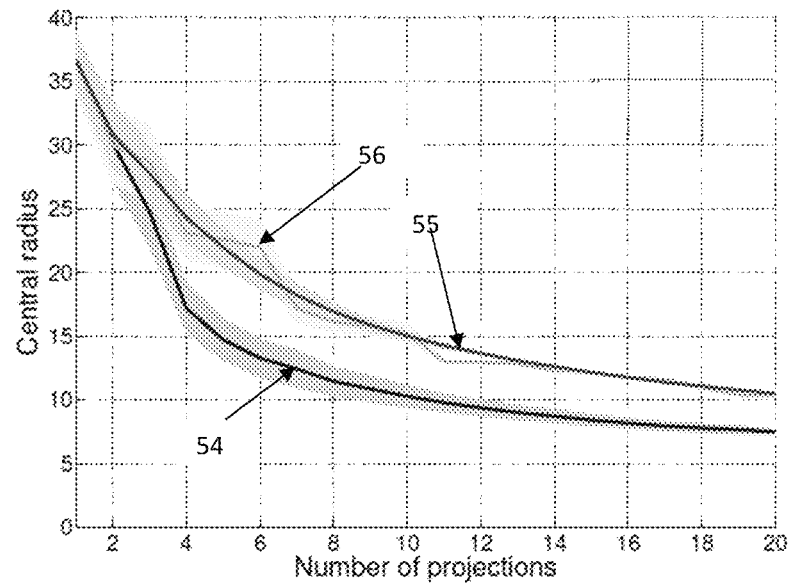
FIG. 17a to FIG. 17d shows graphs of the central radius R as a function of the number of projections d for the four phantoms shown in FIG. 11.
Figure 17B:
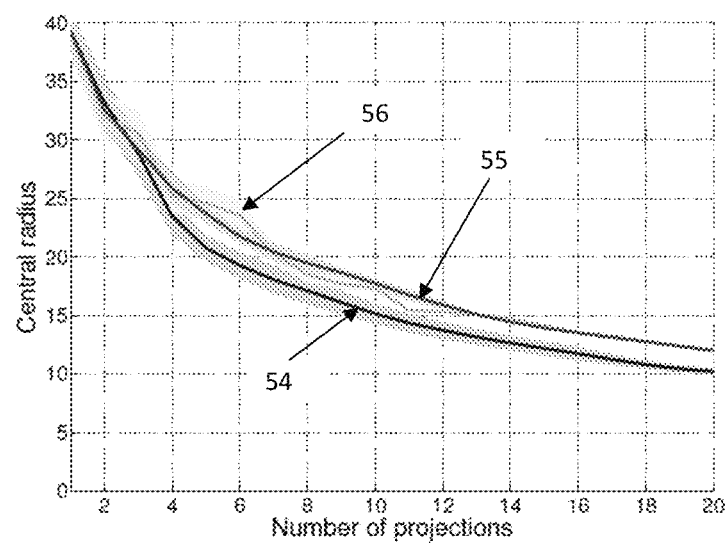
Figure 17C:
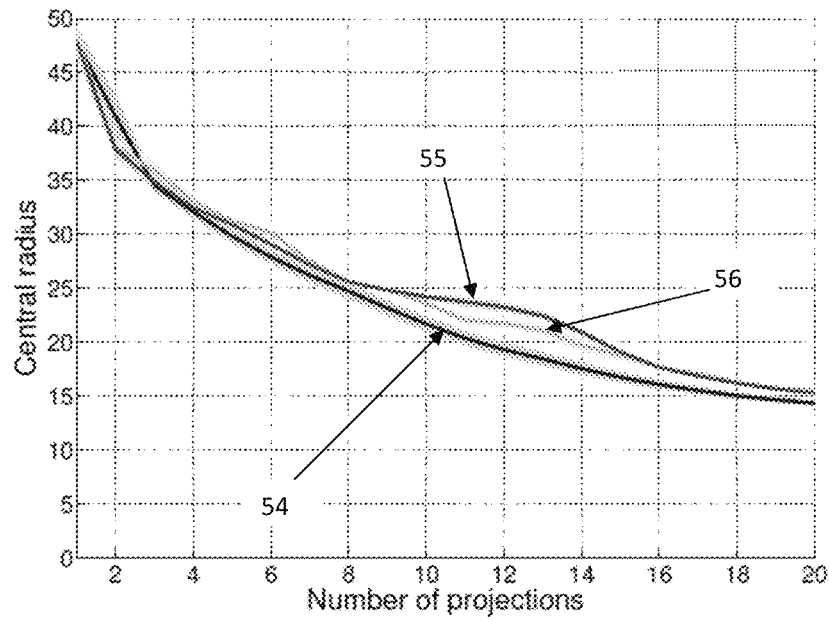
Figure 17D:
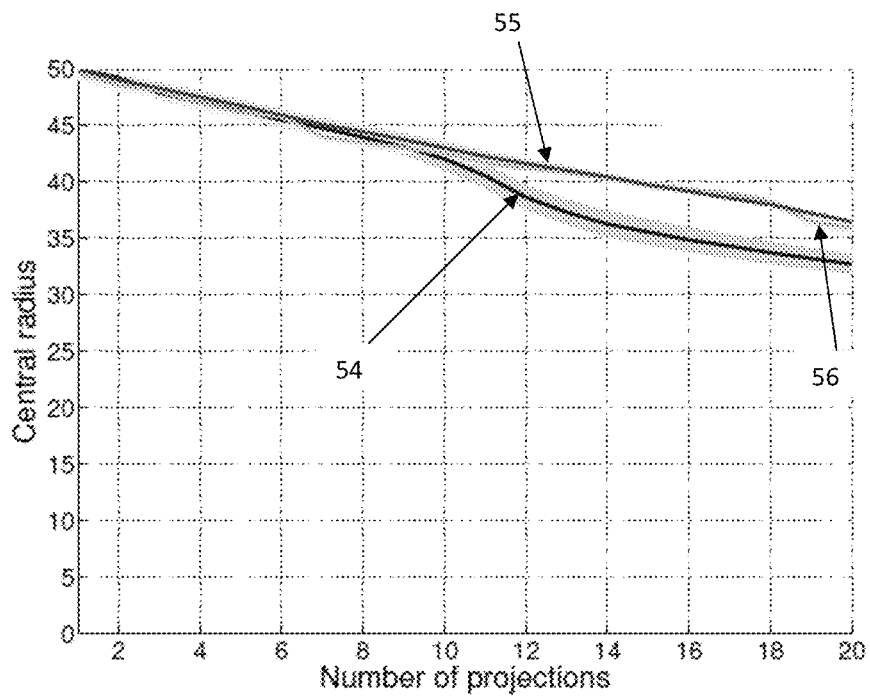

For the more complex phantoms 3 and 4, the number of projections that is needed to reach a reasonable agreement between the Phantom gain and the Sample gain is substantially higher. FIG. 14a to FIG. 14d illustrates the situation for phantom 3, whereby graphs are shown for d=2 (FIG. 14a), d=3 (FIG. 14b), d=4 (FIG. 14c) and d=5 (FIG. 14d). FIG. 15a to FIG. 15d illustrates the situation for phantom 4, whereby subgraphs are shown for d=12 (FIG. 15a), d=14 (FIG. 15b), d=16 (FIG. 15c) and d=18 (FIG. 15d). For Phantom 3, there is a high correlation between both curves for d equal to or higher than 4, whereas 14 projections or more are required to properly localize the "best" projection angle for phantom 4, as can be seen in FIG. 15a to FIG. 15d.

Another observation that can be made, is that for all four phantoms, there is generally a good agreement between the rNMP that is computed with respect to the phantom, and the Phantom gain. Local minima of the rNMP curve tend to correspond with local maxima of the Phantom gain, and vice versa. This correspondence is illustrative for the ability of the dynamic angle selection algorithm to rapidly achieve a high reconstruction quality with respect to the phantom object, even though the phantom is not known to the algorithm.

In the following examples, the selection of a complete sequence of angles is considered, starting with 1 angle and expanding the sequence up to 20 angles. The experiments have been performed using three different angle selection methods. The following three reconstruction methods are compared:

standard: angles are selected between 0° and 180°, with equi-angular spacing. It is to be noted that for this scheme, changing the number of angles actually changes the entire set of selected angles gap-angle: based on the current set of angles, a new angle is selected as the mid-point between the two consecutive angles that have the largest angular gap between them. If several pairs of angles have an equal gap, a uniformly random choice is made.

Dynamic: angles are selected using the dynamic angle selection algorithm according to an embodiment of the present invention. To select an angle, 10 surrogate solutions are generated and their mean information gain is evaluated for all candidate angles, with steps of 1 degree.

For each angle selection method, a series of runs has been performed. For the first angle in the sequence, runs were performed using each multiple of 20 degrees, ranging from 0 degree up to 160 degrees. For each starting angle, the gap-angle and dynamic methods were run 5 times, each using a different random seed.

To reduce the influence of the start angle in the evaluation of the rNMP and central radius, the following strategies were used. For the Standard method using N angles, the first angle was varied between 0 and 180/N. For the Gap angle, the start angel was randomly varied in the range [0, 180]°.

In FIG. 16a to FIG. 16d and FIG. 17a to FIG. 17d, the results of the rNMP and the central radius are plotted as a function of the number of angles selected for all phantom objects. The shaded region denotes the standard deviation originating from repeating the experiments with varying start angles the randomly chosen seed points to generate the surrogate solutions. In each experiment, three different methods are compared: the standard method 55, as described above, the gap-angle based method 56 as described above and the proposed dynamic angular selection method according to an embodiment of the present invention, referred to as "dynamic" 54.

The experimental results for the four phantom images in the example above illustrates that the proposed dynamic angle selection strategy is indeed capable of finding angles for which the reconstructed image is substantially more accurate than for the standard angle selection scheme. It seems that although the central radius provides an upper bound on the diameter of the set of binary solutions, a strategy that aims to reduce this upper bound also reduces the actual reconstruction error with respect to the unknown phantom.

It should also be noted that the proposed angle selection algorithm described in the above example can be made more computational efficient. In the above example, focus was put on the capabilities of the algorithm with respect to reconstruction quality, and on avoiding the exponential time complexity of enumerating the set of binary solutions. However, in the implementation which utilizes a modern GPU for performing the SIRT and CGLS subroutines for the above example, selecting a single angle for an image of size 128×128 takes around 30 seconds if the current number of angles is 4. By far the most computation time is spent in the CGLS subroutine, which computes the central reconstruction within the evaluation of the information gain for a surrogate solution. In the above example this computation was performed for each surrogate solution, and for each angle, it is called around 180K times just to select a single angle, but in some embodiments, the algorithm is made far more efficient by avoiding the complete recomputation of the central radius by using the results from earlier computations.

The example illustrates that embodiments of the present invention using the concepts of information gain can be far more efficient or more advanced than known algorithms. The results also demonstrate that dynamic angle selection is not only useful in the domain of an extremely small number of projection angles (i.e. less than 10). In fact, as illustrated in the example for the more complex Phantom 4, which clearly has a certain "preferential orientation", the dynamic angle selection scheme mainly outperforms the standard method if there are more than 10 projections. This means that the approach can also be useful for angle selection in the reconstruction of quite complex objects, such as trabecular bones, where it is crucial to use as few projection images as possible, due to radiation damage.

The invention claimed is:

1. A method for determining a projection angle for use in tomographic imaging, the method comprising:
    obtaining projection data comprising at least one projection view from at least one projection angle, the at least one projection view being generated by scanning of a test object with a tomographic imaging device;
    providing a plurality of candidate projection angles;
    for each candidate projection angle, calculating a function value indicative of an amount of information that may be gained by adding to said projection data a further projection view generated by scanning of the test object with the tomographic imaging device from said candidate projection angle, wherein the function value is calculated without specific prior knowledge of the test object, the specific prior knowledge being a blueprint image or model for the test object;
    selecting a candidate projection angle from the plurality of candidate projection angles taking into account said function values.

2. A method according to claim 1, wherein said calculating comprises generating a plurality of intermediate reconstructed images.

3. A method according to claim 2, wherein said generating comprises reconstructing said obtained projection data with an iterative tomographic reconstruction algorithm, in which said iterative tomographic reconstruction algorithm iteratively refines a reconstruction image.

4. A method according to claim 3, wherein, in a first iteration of said iterative tomographic reconstruction algorithm, said reconstruction image initially comprises random data or data generated using a pseudorandom number generator algorithm.

5. A method according to claim 2, wherein said calculating further comprises computing a plurality of intermediate projection data for the plurality of intermediate reconstructed images, the projection data for each intermediate reconstructed image comprising a projection view from the candidate projection angle.

6. A method according to claim 5, wherein said calculating comprises calculating and combining a measure for each of the at least one intermediate projection data.

7. A method according to claim 6, wherein said calculating and combining comprises determining a measure indicative of an upper bound to a hypervolume, in the sense of a metric space defined over binary images, encompassing all binary images that adhere to a set of known projections for each of the at least one intermediate projection data.

8. A method according to claim 1, wherein each projection view comprises at least one observation value obtained at least one detection location.

9. A non-transitory computer-readable medium having instructions stored thereon, which, when implemented on a processing unit, cause the processing unit to perform a method for determining a projection angle for use in tomography imaging, the method comprising
    obtaining projection data comprising at least one projection view from at least one projection angle, the at least one projection view being generated by scanning of a test object with a tomographic imaging device;
    providing a plurality of candidate projection angles;
    for each candidate projection angle, calculating a function value indicative of an amount of information that may be gained by adding to said projection data a further projection view generated by scanning of the test object with the tomographic imaging device from said candidate projection angle, wherein the function value is calculated without specific prior knowledge of the test object, the specific prior knowledge being a blueprint image or model for the test object;
    selecting a candidate projection angle from the plurality of candidate projection angles taking into account said function values.

10. A data carrier storing a computer program product according to claim 9.

11. A method comprising the step of transmitting the instructions stored on the computer-readable medium of claim 9 over a wide area network or local area network, which, when implemented on a processing unit, cause the processing unit to perform the method for determining the projection angle for use in tomography imaging.

12. A processor for determining a projection angle for use in tomographic imaging, the processor comprising an input means configured for obtaining projection data comprising at least one projection view from at least one projection angle, the at least one projection view being generated by scanning of a test object with a tomographic imaging device, candidate-projection-angle obtaining means configured for obtaining a plurality of candidate projection angles, a calculator configured for, for each candidate projection angle, calculating a function value indicative of an amount of information that may be gained by adding to said projection data a further projection view generated by scanning of the test object with the tomographic imaging device from said candidate projection angle, wherein the function value is calculated without specific prior knowledge of the test object, the specific prior knowledge being a blueprint image or model for the test object, and a selector configured for selecting a candidate projection angle from the plurality of candidate projection angles taking into account said function values.

13. A processor according to claim 12, the processor furthermore being configured for performing a method for determining a projection angle including:

obtaining projection data comprising at least one projection view from at least one projection angle, the at least one projection view being generated by scanning of a test object with a tomographic imaging device;

providing a plurality of candidate projection angles;

for each candidate projection angle, calculating a function value indicative of an amount of information that may be gained by adding to said projection data a further projection view generated by scanning of the test object with the tomographic imaging device from said candidate projection angle, wherein the function value is calculated without specific prior knowledge of the test object;

selecting a candidate projection angle from the plurality of candidate projection angles taking into account said function values.

14. A tomographic imaging device for tomographic imaging of objects, the tomographic imaging device comprising a processor according to claim 12 configured for determining a projection angle for use in the tomographic imaging.

* * * * *